United States Patent
Carrick

(10) Patent No.: US 7,930,106 B2
(45) Date of Patent: Apr. 19, 2011

(54) QUANTITATIVE METHOD EMPLOYING ADJUSTMENT OF PRE-DEFINED MASTER CALIBRATION CURVES

(75) Inventor: James M. Carrick, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 809 days.

(21) Appl. No.: 11/948,946

(22) Filed: Nov. 30, 2007

(65) Prior Publication Data

US 2008/0133198 A1    Jun. 5, 2008

Related U.S. Application Data

(60) Provisional application No. 60/868,004, filed on Nov. 30, 2006.

(51) Int. Cl.
*G06F 19/00* (2006.01)
*C12Q 1/68* (2006.01)
*C12P 19/34* (2006.01)

(52) U.S. Cl. ............................. 702/19; 435/6; 435/91.2

(58) Field of Classification Search .................. None
See application file for complete search history.

(56) References Cited

U.S. PATENT DOCUMENTS

| | | | |
|---|---|---|---|
| 5,219,727 A | 6/1993 | Wang et al. | |
| 5,554,539 A | 9/1996 | Chadney et al. | |
| 5,837,501 A | 11/1998 | Beumer et al. | |
| 6,066,458 A | 5/2000 | Haaland et al. | |
| 6,277,584 B1 | 8/2001 | Chu et al. | |
| 6,713,297 B2 | 3/2004 | McMillan et al. | |
| 7,831,417 B2 * | 11/2010 | Carrick et al. | 703/2 |
| 2003/0104438 A1 | 6/2003 | Eyre et al. | |

FOREIGN PATENT DOCUMENTS

| EP | 0 623 682 A1 | 11/1994 |
|---|---|---|
| EP | 1 138 784 A2 | 10/2001 |

OTHER PUBLICATIONS

User Bulletin #2, "ABI PRISM 7700 Sequence Detection System,"XP-002346434, 1997, (Internet: URL:http://www.ukl.uni-freiburg.de/core-facility/taqman/user_bulletin_2), pp. 1-36, PE Applied Biosystems, a Division of Perkin Elmer, USA.
Nichols Advantage, IGFBP-3, Catalog #62-7047, 2004, pp. 1-17, Nichols Institute Diagnostics, USA.

* cited by examiner

*Primary Examiner* — John S Brusca
(74) *Attorney, Agent, or Firm* — Michael J. Gilly

(57) ABSTRACT

Methods and kits for preparing and adjusting pre-defined master calibration curves of the type used for quantifying analyte polynucleotides by real-time nucleic acid amplification. Particularly disclosed are methods of preparing one or more master calibration curves on one instrument, and then using those master calibration curves on a different instrument.

83 Claims, 15 Drawing Sheets

QUANTITATIVE METHOD EMPLOYING ADJUSTMENT OF PRE-DEFINED MASTER CALIBRATION CURVES

RELATED APPLICATION

This application claims the benefit of U.S. Provisional Application No. 60/868,004, filed Nov. 30, 2006. The entire disclosure of this prior application is hereby incorporated by reference.

FIELD OF THE INVENTION

The present invention relates to the field of biotechnology. More specifically, the invention relates to quantitation of analyte polynucleotides using nucleic acid amplification, and still more specifically relates to the use of factory-supplied calibration curves and adjustment calibrators for analyzing results from real-time nucleic acid amplification reactions.

BACKGROUND OF THE INVENTION

Methods involving the kinetic analysis of in vitro nucleic acid amplification have become important tools for quantifying analyte polynucleotides. In these procedures, sometimes referred to as "real-time" amplification procedures, the amount of amplicon present in a nucleic acid amplification reaction mixture is monitored as a function of time over the course of the amplification procedure. Fully automated real-time nucleic acid assays require machine executable algorithms capable of analyzing the time-dependent data acquired during the reaction. In this regard, there is a requirement for data processing algorithms that accurately output an amount or concentration of a nucleic acid that would give rise to an observed amplification result.

Difficulties associated with quantifying the absolute amount of a specific nucleic acid target have been appreciated in the patent literature. These difficulties have been attributed to the exponential nature of the amplification process, and the fact that small differences in any of the variables which control the reaction rate, including the length and nucleotide sequence of the primer pairs, can lead to dramatic differences in amplicon yield. Wang et al., in U.S. Pat. No. 5,219,727 described the use of an internal standard that amplified using the same primers that amplified the analyte polynucleotide, and addressed the fact that use of an unrelated cDNA as a standard necessitated a second set of oligonucleotide primers unrelated to the specific target nucleic acid being quantified. According to Wang et al., analyses which use two sets of unrelated primers can only provide a relative comparison of two independent amplification reactions rather than an absolute measure of a nucleic acid target concentration. Others have followed this teaching and employed internal standards that resemble the target of interest by having similar sequences, and by amplifying with a common pair of primers (see published U.S. patent application Ser. No. 10/230,489). Still others have described quantitative methods that rely on determining the efficiency of amplification (see published European Patent Application EP 1138784). Yet another approach has involved determining amplification ratios for control and target sequences (see U.S. Pat. No. 6,066,458).

Yet other approaches have been used both to improve the quality of quantitative results obtained using real-time nucleic acid amplification, and to simplify assay procedures. One approach involves the use of factory-produced calibration curves that can be loaded into a data processing component of an automated analyzer. The use of such calibration curves, sometimes referred to as "stored master curves," advantageously reduces the number of calibration standard reactions that must be supported by manufacturing, and reduces the number of reactions that must be performed by end users. Since the use of a stored master curve makes it unnecessary to create a complete calibration curve every time an assay is performed, the requirement for batch testing that would otherwise employ a contemporaneously generated local calibration plot is eliminated.

The invention described herein provides a mechanism for adjusting stored master calibration curves using results obtained by running only a very small number of calibration standard reactions.

SUMMARY OF THE INVENTION

A first aspect of the invention relates to a method of establishing an equation for an adjusted calibration curve. In accordance with the method, first there is a step for obtaining a plurality of standard samples, each containing a constant starting quantity of an internal calibrator and a known starting quantity of an analyte polynucleotide standard. Next, there is a step for coamplifying the internal calibrator and the analyte polynucleotide standard in each of the plurality of standard samples. Next there is a step for determining for each of the plurality of standard samples indicia of amplification for the internal calibrator and the analyte polynucleotide standard that coamplified. Consequently, there is obtained a collection of determined indicia of amplification for the internal calibrator as a function of the known starting quantity of the analyte polynucleotide standard, and a collection of determined indicia of amplification for the analyte polynucleotide standard as a function of the known starting quantity of the analyte polynucleotide standard. Next, there is a step for optimizing a first equation to fit a first curve to the collection of determined indicia of amplification for the internal calibrator as a function of the known starting quantity of the analyte polynucleotide standard, thereby resulting in a first fitted equation. Additionally, there is a step for optimizing a second equation to fit a second curve to the collection of determined indicia of amplification for the analyte polynucleotide standard as a function of the known starting quantity of the analyte polynucleotide standard, thereby resulting in a second fitted equation. Next, there is a step for obtaining an adjustment calibrator that includes a predetermined quantity of the analyte polynucleotide standard and the constant starting quantity of the internal calibrator. Next, there is a step for coamplifying the internal calibrator and the analyte polynucleotide standard of the adjustment calibrator. This is followed by a step for determining for the adjustment calibrator indicia of amplification for the internal calibrator and the analyte polynucleotide standard that coamplified. Next, there is a step for modifying the first fitted equation using the indicia of amplification determined for the internal calibrator of the adjustment calibrator, whereby there results an adjusted first fitted equation for fitted indicia of amplification for the internal calibrator as a function of the known starting quantity of the analyte polynucleotide standard. There also is a step for modifying the second fitted equation using the indicia of amplification determined for the analyte polynucleotide of the adjustment calibrator, whereby there results an adjusted second fitted equation for fitted indicia of amplification for the analyte polynucleotide standard as a function of the known starting quantity of the analyte polynucleotide standard. Finally, there is a step for establishing the equation for the adjusted calibration curve by mathematically relating to each other the adjusted first fitted equation, and the adjusted second fitted equation. In the context of the invention, "mathematically relating" implies performance of an operation such as addition, subtraction, multiplication or division. The process of division to result in calculation of a ratio is highly preferred. In one generally preferred embodiment, the coamplifying steps involve coamplifying isothermally. This may involve coamplifying isothermally in transcription-associated amplification reactions that include an RNA polymerase. In another generally preferred embodiment, the coamplifying steps are each performed on different instruments. In another generally preferred embodiment, the first coamplifying step involves coamplifying in a nucleic acid amplification reaction performed on a first instrument, and the second coamplifying step involves coamplifying in a nucleic acid amplification reaction performed on a second instrument. When this is the case, the first and second fitted equations of the optimizing steps can be stored in a computer memory device linked to the second instrument. More preferably, the establishing step involves establishing the equation for the adjusted calibration curve for use on the second instrument. In yet another generally preferred embodiment, the first coamplifying step involves coamplifying in an isothermal nucleic acid amplification reaction performed on a first instrument, the second coamplifying step involves coamplifying in an isothermal nucleic acid amplification reaction performed on a second instrument, and the first and second fitted equations of the optimizing steps are stored in a computer memory device linked to the second instrument. In one version of this generally preferred embodiment, the first and second fitted equations of the optimizing steps each include a plurality of coefficients, and the step for obtaining the adjustment calibrator further involves obtaining the plurality of coefficients for the respective first and second fitted equations. In another version of this generally preferred embodiment, the first and second equations of the optimizing steps are non-linear equations, with each having a plurality of coefficients. In one highly preferred embodiment, the process of mathematically relating to each other in the establishing step involves mathematically relating numerical results calculated using the adjusted second fitted equation and numerical results calculated using the adjusted first fitted equation. This may involve the process of division, and so results in the calculation of the ratio. In another highly preferred embodiment, the isothermal nucleic acid amplification reactions of the coamplifying steps each include a primer that amplifies both the analyte polynucleotide standard and the internal calibrator. In another highly preferred embodiment, the isothermal nucleic acid amplification reactions of the coamplifying steps include primers that amplify both the analyte polynucleotide standard and the internal calibrator, and do not include primers that amplify only the analyte polynucleotide standard or the internal calibrator. In another highly preferred embodiment, the isothermal nucleic acid amplification reactions of the coamplifying steps do not include any primer that amplifies both the analyte polynucleotide standard and the internal calibrator. In another highly preferred embodiment, the coamplifying steps result in the synthesis of analyte polynucleotide standard amplicons and internal calibrator amplicons, where the analyte polynucleotide standard amplicons and the internal calibrator amplicons are different lengths. In another highly preferred embodiment, the coamplifying steps result in the synthesis of analyte polynucleotide standard amplicons and internal calibrator amplicons, where the analyte polynucleotide standard amplicons and the internal calibrator amplicons have different percentages of G+C bases. In another generally preferred embodiment, the first fitted equation of the first optimizing step includes a plurality of first fitted equation coefficients, and the second fitted equation of the second optimizing step includes a plurality of second fitted equation coefficients. In another generally preferred embodiment, the process of mathematically relating to each other in the final establishing step involves mathematically relating numerical results calculated using the adjusted second fitted equation and numerical results calculated using the adjusted first fitted equation. This can involve the process of division, and so can result in calculation of a ratio. In another generally preferred embodiment, the process of mathematically relating to each other in the final establishing step involves mathematically relating numerical results calculated using the adjusted second fitted equation and numerical results calculated using the adjusted first fitted equation. This can involve the process of subtraction, and so can result in calculation of a difference. In another generally preferred embodiment, the first modifying step involves determining an adjustment factor for internal calibrator using the indicia of amplification determined for the internal calibrator of the adjustment calibrator, and a value calculated by solving the first fitted equation at the starting quantity of analyte polynucleotide equal to the predetermined quantity of the analyte polynucleotide standard of the adjustment calibrator. This may be followed by a step for adding the adjustment factor for internal calibrator to one coefficient of the first fitted equation. As well, the second modifying step can involve determining an adjustment factor for analyte polynucleotide using the indicia of amplification determined for the analyte polynucleotide standard of the adjustment calibrator, and a value calculated by solving the second fitted equation at the starting quantity of analyte polynucleotide equal to the predetermined quantity of the analyte polynucleotide standard of the adjustment calibrator. This may be followed by a step for adding the adjustment factor for analyte polynucleotide to one coefficient of the second fitted equation. In another generally preferred embodiment, the coamplifying steps each involve coamplifying in a nucleic acid amplification reaction that includes a primer that amplifies both the analyte polynucleotide standard and the internal calibrator. In another generally preferred embodiment, the coamplifying steps each involve coamplifying in a nucleic acid amplification reaction that includes primers that amplify both the analyte polynucleotide standard and the internal calibrator, and does not include primers that amplify only the analyte polynucleotide standard or the internal calibrator. In another generally preferred embodiment, the coamplifying steps each involve coamplifying in a nucleic acid amplification reaction that does not include any primer that amplifies both the analyte polynucleotide standard and the internal calibrator. In another generally preferred embodiment, there are some additional steps. More particularly, there may be a further step for obtaining a second adjustment calibrator that includes a second predetermined quantity of the analyte polynucleotide standard and the constant quantity of the internal calibrator. This may be followed by a step for coamplifying the internal calibrator and the analyte polynucleotide standard of the second adjustment calibrator. Next, there is a step for determining for the second adjustment calibrator indicia of amplification for the internal calibrator and the analyte polynucleotide standard that coamplified. This is followed by a step for modifying the first and second fitted equations using respectively the indicia of amplification for the internal calibrator of the second adjustment calibrator and the analyte polynucleotide standard of the second adjustment calibrator. In another generally preferred embodiment, the coamplifying steps result in the synthesis of an analyte polynucleotide standard amplicon and an internal calibrator amplicon, where the analyte polynucleotide standard amplicon and the internal calibrator amplicon are different lengths. In another generally preferred embodiment, the coamplifying steps result in the synthesis of an analyte polynucleotide standard amplicon and an internal calibrator amplicon, where the analyte polynucleotide standard amplicon and the internal calibrator amplicon have different percentages of G+C bases. In another generally preferred embodiment, the first and second equations of the optimizing steps are non-linear equations, each having a plurality of coefficients. In yet another generally preferred embodiment, the first and second fitted equations of the optimizing steps each have a plurality of coefficients, and the step for obtaining the adjustment calibrator further involves obtaining the respective plurality of coefficients for the first and second fitted equations.

A second aspect of the invention relates to a method of preparing a kit that includes a calibrator for adjusting a stored master calibration curve. In accordance with the method, first there is a step for forming a plurality of standard samples, each containing a constant starting quantity of an internal calibrator and a known starting quantity of an analyte polynucleotide standard. Next, there is a step for coamplifying the internal calibrator and the analyte polynucleotide standard in a nucleic acid amplification reaction for each of the plurality of standard samples. Next, there is a step for determining indicia of amplification for the internal calibrator and the analyte polynucleotide standard that coamplified in each nucleic acid amplification reaction, whereby there is obtained a collection of determined indicia of amplification for the internal calibrator as a function of the known starting quantity of the analyte polynucleotide standard, and a collection of determined indicia of amplification for the analyte polynucleotide standard as a function of the known starting quantity of the analyte polynucleotide standard. This is followed by a step for optimizing a first equation to fit a first curve to the collection of determined indicia of amplification for the internal calibrator as a function of the known starting quantity of the analyte polynucleotide standard, thereby resulting in a first fitted equation comprising a set of first fitted equation coefficients. There also is a step for optimizing a second equation to fit a second curve to the collection of determined indicia of amplification for the analyte polynucleotide standard as a function of the known starting quantity of the analyte polynucleotide standard, thereby resulting in a second fitted equation comprising a set of second fitted equation coefficients. Finally, there is a step for preparing a packaged combination that includes: (a) a tangible form of the set of first fitted equation coefficients, (b) a tangible form of the set of second fitted equation coefficients, and (c) an adjustment calibrator having a predetermined amount of the analyte polynucleotide standard, and the constant starting quantity of the internal calibrator. In one generally preferred embodiment, the nucleic acid amplification reaction of the coamplifying step is an isothermal nucleic acid amplification reaction. For example, this may involve coamplifying isothermally in a transcription-associated amplification reaction that includes an RNA polymerase. In another generally preferred embodiment, the nucleic acid amplification reaction of the coamplifying step includes a primer that amplifies both the analyte polynucleotide standard and the internal calibrator. In another generally preferred embodiment, the nucleic acid amplification reaction of the coamplifying step includes primers that amplify both the analyte polynucleotide standard and the internal calibrator, and do not include primers that amplify only the analyte polynucleotide standard or the internal calibrator. In another generally preferred embodiment, the nucleic acid amplification reaction of the coamplifying step does not include any primer that amplifies both the analyte polynucleotide standard and the internal calibrator. In another generally preferred embodiment, the step for determining indicia of amplification involves determining time-dependent indicia of amplification. In another generally preferred embodiment, the first and second equations of the optimizing steps are first and second non-linear equations. In another generally preferred embodiment, the tangible forms of the sets of first and second fitted equation coefficients are machine-readable forms of the sets of first and second fitted equation coefficients. For example, the machine-readable forms of the sets of first and second fitted equation coefficients may involve a barcode. In another generally preferred embodiment, the coamplifying step produces an internal calibrator amplicon and an analyte polynucleotide standard amplicon, where the internal calibrator amplicon and the analyte polynucleotide standard amplicon are different lengths. In another generally preferred embodiment, the coamplifying step produces an internal calibrator amplicon and an analyte polynucleotide standard amplicon, where the internal calibrator amplicon and the analyte polynucleotide standard amplicon have different percentages of G+C bases. In another generally preferred embodiment, the packaged combination of the preparing step further includes a second adjustment calibrator that has a second predetermined starting quantity of the analyte polynucleotide standard and the same constant starting quantity of the internal calibrator. In another generally preferred embodiment, the nucleic acid amplification reaction of the coamplifying step is an isothermal nucleic acid amplification reaction, and the first and second equations of the optimizing steps are first and second non-linear equations. In one highly preferred embodiment, the nucleic acid amplification reaction of the coamplifying step includes a primer that amplifies both the analyte polynucleotide standard and the internal calibrator. In another highly preferred embodiment, the nucleic acid amplification reaction of the coamplifying step includes primers that amplify both the analyte polynucleotide standard and the internal calibrator, and does not include primers that amplify only the analyte polynucleotide standard or the internal calibrator. In another highly preferred embodiment, the nucleic acid amplification reaction of the coamplifying step does not include any primer that amplifies both the analyte polynucleotide standard and the internal calibrator. In another highly preferred embodiment, the coamplifying step produces an internal calibrator amplicon and an analyte polynucleotide standard amplicon, where the internal calibrator amplicon and the analyte polynucleotide standard amplicon have different percentages of G+C bases. In another highly preferred embodiment, the coamplifying step produces an internal calibrator amplicon and an analyte polynucleotide standard amplicon, where the internal calibrator amplicon and the analyte polynucleotide standard amplicon are different lengths. Still more preferably, the nucleic acid amplification reaction of the coamplifying step includes a primer that amplifies both the analyte polynucleotide standard and the internal calibrator. Alternatively, the nucleic acid amplification reaction of the coamplifying step includes primers that amplify both the analyte polynucleotide standard and the internal calibrator, and does not comprise primers that amplify only the analyte polynucleotide standard or the internal calibrator. In accordance with yet another alternative, the nucleic acid amplification reaction of the coamplifying step does not include any primer that amplifies both the analyte polynucleotide standard and the internal calibrator.

A third aspect of the invention relates to a method of preparing an equation for quantifying analyte polynucleotide in multiplex nucleic acid amplification reactions that include a constant amount of internal calibrator. In accordance with the method, first there is a step for obtaining a plurality of coefficients of a first stored master curve equation that specifies indicia of amplification for analyte polynucleotide standard as a function of the starting quantity of analyte polynucleotide standard input into nucleic acid amplification reactions. Next, there is a step for obtaining a plurality of coefficients of a second stored master curve equation that specifies indicia of amplification for internal calibrator as a function of the starting quantity of analyte polynucleotide standard input into nucleic acid amplification reactions. Next, there is a step for performing a nucleic acid amplification reaction using an adjustment calibrator that comprises a known amount of analyte polynucleotide standard and the constant starting amount of internal calibrator, wherein the nucleic acid amplification reaction coamplifies analyte polynucleotide standard and internal calibrator of the adjustment calibrator, and wherein the nucleic acid amplification reaction produces an analyte polynucleotide standard amplicon and an internal calibrator amplicon. Next, there is a step for determining indicia of amplification for analyte polynucleotide standard and internal calibrator that coamplified in the nucleic acid amplification reaction. Next, there is a step for establishing an adjustment factor for analyte polynucleotide standard using indicia of amplification for analyte polynucleotide standard determined from the nucleic acid amplification reaction, and a value calculated by solving the first stored master curve equation at the starting quantity of analyte polynucleotide standard equal to the known amount of analyte polynucleotide standard of the adjustment calibrator. There also is a step for establishing an adjustment factor for internal calibrator using indicia of amplification for internal calibrator determined from the nucleic acid amplification reaction, and a value calculated by solving the second stored master curve equation at the starting quantity of analyte polynucleotide standard equal to the known amount of analyte polynucleotide standard of the adjustment calibrator. Next, there is a step for modifying one coefficient of the first stored master curve equation using the adjustment factor for analyte polynucleotide standard, whereby there results an equation specifying an adjusted calibration curve for analyte polynucleotide standard. There also is a step for modifying one coefficient of the second stored master curve equation using the adjustment factor for internal calibrator, whereby there results an equation specifying an adjusted calibration curve for internal calibrator. Finally, there is a step for preparing the equation for quantifying analyte polynucleotide by mathematically relating to each other (a) the equation specifying the adjusted calibration curve for analyte polynucleotide standard, and (b) the equation specifying the adjusted calibration curve for internal calibrator. In one generally preferred embodiment, the step for performing the nucleic acid amplification reaction involves performing an isothermal nucleic acid amplification reaction. This may involve coamplifying isothermally in a transcription-associated amplification reaction that includes an RNA polymerase. In another generally preferred embodiment, the analyte polynucleotide standard amplicon and the internal calibrator amplicon of the performing step are different lengths. In another generally preferred embodiment, the analyte polynucleotide standard amplicon and the internal calibrator amplicon of the performing step have different percentages of G+C bases. In another generally preferred embodiment, the performing step involves performing on a first nucleic acid amplification instrument the nucleic acid amplification reaction, and the plurality of coefficients of the first stored master curve equation and the plurality of coefficients of the second stored master curve equation of the steps for obtaining are not determined using the first nucleic acid amplification instrument. Stated differently, the coefficients were determined using results from amplification reactions carried out on an instrument different from the first instrument. In another generally preferred embodiment, the step for determining indicia of amplification involves determining time-dependent indicia of amplification. In another generally preferred embodiment, the first and second stored master curve equations are non-linear equations. In another generally preferred embodiment, the nucleic acid amplification reaction of the performing step includes at least one primer that amplifies both internal calibrator and analyte polynucleotide standard. In another generally preferred embodiment, the nucleic acid amplification reaction of the performing step includes shared primers, and does not include any primer that amplifies internal calibrator without also amplifying analyte polynucleotide standard. In another generally preferred embodiment, the nucleic acid amplification reaction of the performing step does not include any shared primer that amplifies both internal calibrator and analyte polynucleotide standard. In another generally preferred embodiment, the step for preparing the equation for quantifying analyte polynucleotide involves mathematically relating by the process of division to determine a ratio. In another generally preferred embodiment, the step for preparing the equation for quantifying analyte polynucleotide involves mathematically relating by subtraction to determine a difference. Generally speaking, when the step for preparing the equation for quantifying analyte polynucleotide involves mathematically relating by the process of division to determine a ratio, the step for performing the nucleic acid amplification reaction may include performing an isothermal nucleic acid amplification reaction, and the first and second stored master curve equations can be non-linear equations. In one highly preferred embodiment, the nucleic acid amplification reaction of the performing step includes at least one primer that amplifies both internal calibrator and analyte polynucleotide standard. In another highly preferred embodiment, the nucleic acid amplification reaction of the performing step includes shared primers, and does not include any primer that amplifies internal calibrator without also amplifying analyte polynucleotide standard. In another highly preferred embodiment, the nucleic acid amplification reaction of the performing step does not include any shared primer that amplifies both internal calibrator and analyte polynucleotide standard. In another highly preferred embodiment, the analyte polynucleotide standard amplicon and the internal calibrator amplicon of the step for performing the nucleic acid amplification reaction have different percentages of G+C bases. In another highly preferred embodiment, the analyte polynucleotide standard amplicon and the internal calibrator amplicon of the step for performing the nucleic acid amplification reaction have different lengths. Still more preferably, the nucleic acid amplification reaction of the performing step includes at least one primer that amplifies both internal calibrator and analyte polynucleotide standard. Alternatively, the nucleic acid amplification reaction of the performing step includes shared primers, and does not include any primer that amplifies internal calibrator without also amplifying analyte polynucleotide standard. In accordance with yet another alternative, the nucleic acid amplification reaction of the performing step does not include any shared primer that amplifies both internal calibrator and analyte polynucleotide standard. In another generally preferred embodiment, the step for preparing the equation for quantifying analyte polynucleotide involves mathematically relating numerical values calculated using the equation specifying the adjusted calibration curve for analyte polynucleotide standard, and numerical values calculated using the equation specifying the adjusted calibration curve for internal calibrator. In accordance with one alternative, the step for preparing the equation for quantifying analyte polynucleotide involves mathematically relating by the process of division to calculate a ratio. In accordance with another alternative, the step for preparing the equation for quantifying analyte polynucleotide involves mathematically relating by subtraction to calculate a difference. In another generally preferred embodiment, the step for performing the nucleic acid amplification reaction involves performing an isothermal nucleic acid amplification reaction, and the first and second stored master curve equations are non-linear equations. In one highly preferred embodiment, the nucleic acid amplification reaction of the performing step includes at least one primer that amplifies both internal calibrator and analyte polynucleotide standard. In another highly preferred embodiment, the nucleic acid amplification reaction of the performing step includes shared primers, and does not comprise any primer that amplifies internal calibrator without also amplifying analyte polynucleotide standard. In another highly preferred embodiment, the nucleic acid amplification reaction of the performing step does not include any shared primer that amplifies both internal calibrator and analyte polynucleotide standard. In another highly preferred embodiment, the analyte polynucleotide standard amplicon and the internal calibrator amplicon of the step for performing the nucleic acid amplification reaction have different percentages of G+C bases. In another highly preferred embodiment, the analyte polynucleotide standard amplicon and the internal calibrator amplicon of the step for performing the nucleic acid amplification reaction have different lengths. When this is the case, the nucleic acid amplification reaction of the step for performing can include at least one primer that amplifies both internal calibrator and analyte polynucleotide standard. Alternatively, the nucleic acid amplification reaction of the performing step includes shared primers, and does not include any primer that amplifies internal calibrator without also amplifying analyte polynucleotide standard. In accordance with yet another alternative, the nucleic acid amplification reaction of the performing step does not include any shared primer that amplifies both internal calibrator and analyte polynucleotide standard.

BRIEF DESCRIPTION OF THE DRAWINGS

FIG. 2A shows the indica of amplification (i.e., y-axis representing TTime values measured in minutes) for the internal calibrator signal plotted against the log copy level of the analyte polynucleotide contained in a collection of calibration standards (x-axis). Data points plotted in FIG. 2A are the same as those plotted in FIG. 1. FIG. 2B shows the indica of amplification (i.e., y-axis representing TTime values measured in minutes) for the analyte polynucleotide signal plotted against the log copy level of the analyte polynucleotide contained in a collection of calibration standards (x-axis). Results presented in these graphs were obtained using four different instruments for performing and monitoring amplicon production as a function of time.

FIG. 3A illustrates the master calibration curve for the internal calibrator, the results for amplification reactions conducted using two different adjustment calibrators (i.e., Cal_1(IC) and Cal_2(IC)), and the difference between the predicted and measured indicia of amplification for each of the two adjustment calibrators ($\Delta$Cal_1 (IC) and $\Delta$Cal_2(IC)). FIG. 3B illustrates the master calibration curve for internal calibrator, the results for amplification reactions conducted using the two different adjustment calibrators (i.e., Cal_1(IC) and Cal_2(IC)), and the position of the adjusted master calibration curve for internal calibrator. FIG. 3C illustrates the master calibration curve for analyte polynucleotide, the results for amplification reactions conducted using two different adjustment calibrators (Cal_1 (analyte) and Cal_2(analyte)), and the position of the adjusted master calibration curve for analyte polynucleotide.

DEFINITIONS

Figure 1:
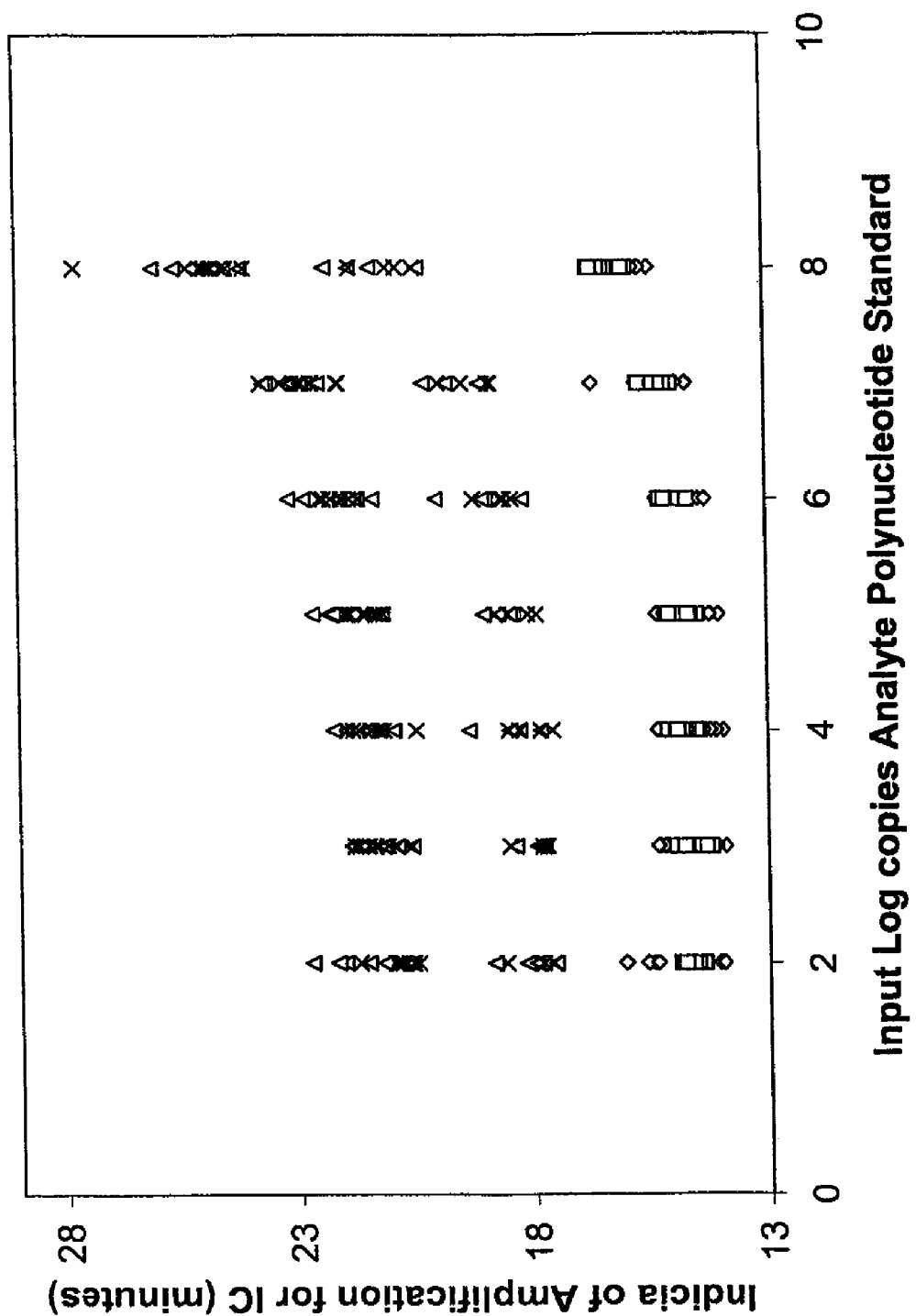
FIG. 1 is a graphic plot showing results from a series of isothermal transcription-associated nucleic acid amplification reactions conducted and monitored on four different amplification/detection instruments. Data points shown on the plot indicate the indicia of amplification (i.e., TTime values measured in minutes) for the internal calibrator on the y-axis at different levels of input analyte polynucleotide standard (i.e., x-axis) for instrument 1 ($\diamond$), instrument 2 ($\square$), instrument 3 ($\Delta$) and instrument 4 (X).

The following terms have the following meanings for the purpose of this disclosure, unless expressly stated to the contrary herein.

As used herein, "polynucleotide" means either RNA, DNA, or a chimeric molecule containing both RNA and DNA. The term also embraces molecules containing nucleotide analogs of RNA or DNA.

By "analyte polynucleotide" or "analyte nucleic acid" is meant a polynucleotide of interest that is to be quantified.

As used herein, a "test sample" is any sample to be investigated for the presence of a particular polynucleotide species. Test samples include any tissue or polynucleotide-containing material obtained from a human, animal, environmental, or laboratory-derived or synthetic sample.

As used herein, "standard samples" are samples containing an analyte polynucleotide standard.

By "analyte polynucleotide standard" is meant a known quantity of an analyte polynucleotide, or fragment thereof. For example, an HIV-1 analyte polynucleotide standard may contain a known number of copies of an HIV-1 genome, HIV-1 transcript, or in vitro synthesized transcript representing a portion of the viral genome.

An "amplicon" is a polynucleotide product of an amplification reaction wherein a target nucleic acid sequence served as the template for synthesis of polynucleotide copies or amplification products.

By "amplification" or "nucleic acid amplification" or "in vitro nucleic acid amplification" is meant any known procedure for obtaining multiple copies, allowing for RNA and DNA equivalents, of a target nucleic acid sequence or its complement or fragments thereof. Amplification of "fragments thereof" refers to production of an amplified nucleic acid containing less than the complete target region nucleic acid sequence or its complement. Such fragments may be produced by amplifying a portion of the target nucleic acid, for example, by using an amplification oligonucleotide which hybridizes to, and initiates polymerization from, an internal position of the target nucleic acid.

As used herein, the terms "coamplify" and "coamplifying" and variants thereof refer to a process wherein different target nucleic acid sequences are amplified in a single amplification reaction. For example, an analyte polynucleotide and an unrelated internal calibrator nucleic acid are "coamplified" when both nucleic acids are amplified in reactions taking place in a single tube, and when both amplification reactions share at least one reagent (e.g., deoxyribonucleotide triphosphates, enzyme, primer(s), etc.) in common.

As used herein, "thermal cycling" refers to repeated changes of temperature, (i.e., increases or decreases of temperature) in a reaction mixture. Samples undergoing thermal cycling may shift from one temperature to another, stabilize at that temperature, transition to a second temperature or return to the starting temperature. The temperature cycle may be repeated as many times as required to study or complete the particular chemical reaction of interest.

By "target nucleic acid" or "target" is meant a nucleic acid containing a target nucleic acid sequence. In general, a target nucleic acid sequence that is to be amplified will be positioned between two oppositely disposed oligonucleotides, and will include the portion of the target nucleic acid that is complementary to each of the oligonucleotides.

By "target nucleic acid sequence" or "target sequence" or "target region" is meant a specific deoxyribonucleotide or ribonucleotide sequence comprising all or part of the nucleotide sequence of a single-stranded nucleic acid molecule, and the deoxyribonucleotide or ribonucleotide sequence complementary thereto.

By "transcription-associated amplification" is meant any type of nucleic acid amplification that uses an RNA polymerase to produce multiple RNA transcripts from a nucleic acid template. Conventionally, these amplification reactions employ at least one primer having a 3'-end that can be extended by the activity of a DNA polymerase. One example of a transcription-associated amplification method, called "Transcription Mediated Amplification" (TMA), generally employs an RNA polymerase, a DNA polymerase, deoxyribonucleoside triphosphates, ribonucleoside triphosphates, and a promoter-containing oligonucleotide complementary to the target nucleic acid. Variations of TMA are well known in the art as disclosed in detail in Burg et al., U.S. Pat. No. 5,437,990; Kacian et al., U.S. Pat. Nos. 5,399,491 and 5,554,516; Kacian et al., PCT No. WO 93/22461; Gingeras et al., PCT No. WO 88/01302; Gingeras et al., PCT No. WO 88/10315; Malek et al., U.S. Pat. No. 5,130,238; Urdea et al., U.S. Pat. Nos. 4,868,105 and 5,124,246; McDonough et al., PCT No. WO 94/03472; and Ryder et al., PCT No. WO 95/03430. Other transcription-associated amplification methods employing only a single primer that can be extended by a DNA polymerase, as disclosed in the U.S. patent application having Ser. No. 11/213,519 are particularly embraced by the definition and are highly preferred for use in connection with the method disclosed herein.

As used herein, an "oligonucleotide" or "oligomer" is a polymeric chain of at least two, generally between about five and about 100, chemical subunits, each subunit comprising a nucleotide base moiety, a sugar moiety, and a linking moiety that joins the subunits in a linear spacial configuration. Common nucleotide base moieties are guanine (G), adenine (A), cytosine (C), thymine (T) and uracil (U), although other rare or modified nucleotide bases able to hydrogen bond are well known to those skilled in the art. Oligonucleotides may optionally include analogs of any of the sugar moieties, the base moieties, and the backbone constituents. Preferred oligonucleotides of the present invention fall in a size range of about 10 to about 100 residues. Oligonucleotides may be purified from naturally occurring sources, but preferably are synthesized using any of a variety of well known enzymatic or chemical methods.

By "amplification oligonucleotide" or "amplification oligomer" is meant an oligomer that hybridizes to a target nucleic acid, or its complement, and participates in a nucleic acid amplification reaction. Examples of amplification oligomers include primers that contain a 3' end that is extended as part of the amplification process, but also include oligomers that are not extended by a polymerase (e.g., a 3' blocked oligomer) but may participate in, or facilitate efficient amplification from a primer. Preferred size ranges for amplification oligomers include those that are about 10 to about 80 nt long, or 10 to about 60 nt long and contain at least about 10 contiguous bases, and more preferably at least 12 contiguous bases that are complementary to a region of the target nucleic acid sequence (or a complementary strand thereof). The contiguous bases are preferably at least about 80%, more preferably at least about 90%, and most preferably about 100% complementary to the target sequence to which amplification oligomer binds. An amplification oligomer may optionally include modified nucleotides or analogs, or additional nucleotides that participate in an amplification reaction but are not complementary to or contained in the target nucleic acid. An amplification oligomer that is 3' blocked but capable of hybridizing to a target nucleic acid and providing an upstream promoter sequence that serves to initiate transcription is referred to as a "promoter provider" oligomer.

A "primer" is an amplification oligomer that hybridizes to a template nucleic acid and has a 3' OH end that can be extended by a DNA polymerase. The 5' region of the primer may be non-complementary to the target nucleic acid (e.g., a promoter sequence), resulting in an oligomer referred to as a "promoter-primer." Those skilled in the art will appreciate that any oligomer that can function as a primer can be modified to include a 5' promoter sequence, and thus could function as a promoter-primer. Similarly, any promoter-primer can be modified by removal of, or synthesis without, a promoter sequence and still function as a primer.

As used herein, a "set" of amplification oligonucleotides refers to a collection of two or more amplification oligonucleotides that cooperatively participate in an in vitro nucleic acid amplification reaction to synthesize amplicons.

As used herein, a "probe" is an oligonucleotide that hybridizes specifically to a target sequence in a nucleic acid, preferably in an amplified nucleic acid, under conditions that promote hybridization, to form a detectable hybrid.

As used herein, "time-dependent" monitoring of nucleic acid amplification, or monitoring of nucleic acid amplification in "real-time" refers to a process wherein the amount of amplicon present in a nucleic acid amplification reaction is measured as a function of reaction time or cycle number and then used to determine a starting amount of template that was present in the reaction mixture at the time the amplification reaction was initiated. For example, the amount of amplicon can be measured prior to commencing each complete cycle of an amplification reaction that comprises thermal cycling, such as PCR. Alternatively, isothermal amplification reactions that do not require physical intervention to initiate the transitions between amplification cycles can be monitored continuously, or at regular time intervals to obtain information regarding the amount of amplicon present as a function of time.

As used herein, a "growth curve" refers to the characteristic pattern of appearance of a synthetic product, such as an amplicon, in a reaction as a function of time or cycle number. A growth curve is conveniently represented as a two-dimensional plot of time (x-axis) against some indicator of product amount, such as a fluorescence measurement (y-axis). Some, but not all, growth curves have a sigmoid-shape.

As used herein, the "baseline phase" of a growth curve refers to the initial phase of the curve wherein the amount of product (such as an amplicon) increases at a substantially constant rate, this rate being less than the rate of increase characteristic of the growth phase (which may have a log-linear profile) of the growth curve. The baseline phase of a growth curve typically has a very shallow slope, frequently approximating zero.

As used herein, the "growth phase" of a growth curve refers to the portion of the curve wherein the measurable product substantially increases with time. Transition from the baseline phase into the growth phase in a typical nucleic acid amplification reaction is characterized by the appearance of amplicon at a rate that increases with time. Transition from the growth phase to the plateau phase of the growth curve begins at an inflection point where the rate of amplicon appearance begins to decrease.

As used herein, the "plateau phase" of a triphasic growth curve refers to the final phase of the curve. In the plateau phase, the rate of measurable product formation generally is substantially lower than the rate of amplicon production in the log-linear phase, and may even approach zero.

As used herein, the phrase "indicia of amplification" refers to features of real-time run curves which indicate a predetermined level of progress in nucleic acid amplification reactions. Such indicia are commonly determined by mathematical analysis of run curves, sometimes referred to as "growth curves," which display a measurable signal (such as a fluorescence reading) whose intensity is related to the quantity of an amplicon present in a reaction mixture as a function of time, cycle number, etc.

As used herein, the phrase "threshold-based indicia of amplification" refers to indicia of amplification that measure the time or cycle number when a growth curve signal crosses an arbitrary value or threshold. TTime determinations are examples of threshold-based indicia of amplification, while TArc and OTArc determinations are examples of non-threshold-based indicia of amplification.

As used herein, the phrase "time-dependent" indicia of amplification refers generally to indicia of amplification (e.g., a reaction progress parameter) that are measured in time units (e.g., minutes). Time-dependent indicia of amplification are commonly used for monitoring progress in isothermal nucleic acid amplification reactions that are not characterized by distinct "cycles." All of TTime, TArc and OTArc are examples of time-dependent indicia of amplification.

By "nucleic acid calibrator" or "internal calibrator" is meant a polynucleotide that is capable of amplification in an in vitro nucleic acid amplification reaction, and that is distinguishable from an analyte polynucleotide coamplified in the same amplification reaction. In certain preferred embodiments, the internal calibrator and the analyte polynucleotide are coamplified in an in vitro nucleic acid amplification reaction using one or more different amplification oligomers or primers. For example, the analyte and internal calibrator polynucleotides employed in the working Examples detailed below were amplified using amplification oligonucleotides that were not shared. In other preferred embodiments, the internal calibrator and the analyte polynucleotide are coamplified in an in vitro nucleic acid amplification reaction using identical amplification oligomers or primers.

As used herein, "internal calibration adjustment" refers to a quantitative procedure for determining the starting amount of analyte nucleic acid in a test sample that underwent amplification by comparison with results obtained for a coamplified target nucleic acid referred to as a "nucleic acid calibrator" or "internal calibrator."

As used herein, the phrase "as a function of" describes the relationship between a dependent variable (i.e., a variable that depends on one or more other variables) and an independent variable (i.e., a variable that may have its value freely chosen without considering the values of any other variables), wherein each input value for the independent variable relates to exactly one output value for the dependent variable. Conventional notation for an equation that relates a y-value (i.e., the dependent variable) "as a function of" an x-value (i.e., the independent variable) is $y=f(x)$.

As used herein, "optimizing" an equation refers to a process, as commonly practiced in mathematical modeling or curve fitting procedures, for obtaining numerical values for coefficients in an equation to yield an expression that "fits" or approximates experimental measurements. Typically, an optimized equation will define a best-fit curve.

As used herein, the terms "optimized equation," and "fitted equation" are alternative references to an equation containing fixed numerical values for coefficients as the result of an optimizing procedure.

As used herein, "incremental" values refer to values that increase or decrease gradually by regular degrees.

As used herein, an "iterative" computing method attempts to solve a problem (e.g., an equation or system of equations) by successive approximations to the solution.

By "calibration standard" is meant a composition that includes a known or predetermined amount analyte polynucleotide standard in combination with a known constant amount of an internal calibrator polynucleotide. Two different calibration standards can contain different amounts of analyte polynucleotide or a fragment thereof, but will contain the same amount of internal calibrator nucleic acid. "Adjustment calibrators" are calibration standards used for conducting amplification reactions that provide data for adjusting a stored master curve (i.e., so that an end user's system can be adjusted to give the same calibrated output as that of the system used to derive the master calibration curve).

By "kit" is meant a packaged combination of materials, typically intended for use in conjunction with each other. Kits in accordance with the invention may include instructions or other information in a "tangible" form (e.g., printed information, electronically recorded on a computer-readable medium, or otherwise recorded on a machine-readable medium such as a barcode for storing numerical values).

By "consisting essentially of" is meant that additional component(s), composition(s) or method step(s) that do not materially change the basic and novel characteristics of the present invention may be included in the present invention. Any component(s), composition(s), or method step(s) that have a material effect on the basic and novel characteristics of the present invention would fall outside of this term.

DETAILED DESCRIPTION OF THE INVENTION

Introduction and Overview

Herein there are disclosed methods for simplifying the quantitation of analyte polynucleotides using real-time nucleic acid amplification techniques. More specifically, the invention relates to methods of making a master calibration curve using real-time amplification results obtained on one or more instruments, and then using that master calibration curve to quantify an analyte polynucleotide by assessing real-time amplification results obtained on a different instrument. This preferably is accomplished by adjusting one or more master calibration curves. The procedure reduces the need for performing an extensive set of nucleic acid amplification reactions to generate a complete calibration curve each time a different assay is performed. This effectively increases throughput of test samples, simplifies assay manufacturing, and saves on the cost on materials.

Development of the disclosed method of adjusting a stored master calibration curve was made possible by the finding that the shapes of two-dimensional calibration curves generated using different instruments to perform and monitor the amplification reactions were substantially similar, except for a vertical shift on the axis representing time-dependent indicia of amplification (e.g., threshold-based TTime values measured in time units). For example, FIG. 1 illustrates results for indicia of amplification for internal calibrator obtained using different instruments for performing and monitoring real-time nucleic acid amplification reactions. Each data point on the plot represents a result from a single amplification reaction performed using a constant starting amount of nucleic acid calibrator and a known amount of analyte polynucleotide standard on one of four different instruments represented by the different symbols ($\Diamond$, $\square$, X, $\Delta$). Visual inspection of the plot revealed that the results clustered so that the general trend among data points representing the indicia of amplification as a function of the number of input log copies of analyte polynucleotide standard was substantially similar for the different instruments. Although not shown in the figure, a curve fitted to the collection of data points for one instrument was substantially similar to curves fitted to the collection of data points for different instruments, except for a shift on the vertical axis of the plot. This was particularly true when the amount of analyte polynucleotide standard used in the amplification reactions fell in the range of from about $10^2$-$10^6$ copies/ml of test sample.

Generally speaking, the disclosed methods are useful for analyzing real-time nucleic acid amplification reactions that yield calibration curves having substantially similar shapes when assays are performed on different instruments—except for a shift of the curve in the dimension related to the indicia of amplification. More specifically, the methods are applicable to analysis of assays that reliably produce a calibration curve of substantially similar shape on a plot of the indicia of amplification (e.g., y-axis) against the amount of input analyte polynucleotide standard (e.g., x-axis), except for the elevation of the curve on the axis representing the indicia of amplification. Thus, adjustment of a stored master calibration curve(s) involved only upward or downward translation of the curve, and did not require adjustment of curve shape. Indeed, the shape of the stored master calibration curve(s) preferably is not changed by the present adjustment procedure which is intended to be performed on a device operated by an end-user. However, as indicated below, the shape of a calibration curve that relates two master calibration curves (i.e., one for analyte polynucleotide standard and another for internal calibrator) to each other by a mathematical operation advantageously can be changed by the adjustment procedure disclosed herein. It is preferred that the curve adjustment procedure not involve translation or shifting of the curve in the dimension corresponding to the input analyte polynucleotide amount used in the standard amplification reactions (e.g., the x-axis).

The methods described herein are useful in connection with amplification-based nucleic acid assays that yield calibration curves having substantially similar shaped curves when reactions are performed on different instruments. In some generally preferred instances, the methods are used in connection with amplification reactions that do not use temperature cycling to achieve nucleic acid amplification. Indeed, in some generally preferred instances, the methods are used in connection with isothermal nucleic acid amplification reactions. In highly preferred instances the methods are used in connection with isothermal transcription-associated amplification reactions.

Advantageously, the methods disclosed herein were highly tolerant of variability in amplification efficiencies of the analyte polynucleotide and the co-amplifiable internal calibrator. Additionally, there was no requirement for the analyte polynucleotide or analyte standard and the internal calibrator to amplify using a shared primer or shared set of primers.

Notably, there is flexibility in the selection of primers used in the coamplification reactions that can be processed by the disclosed quantitative procedures. In one generally preferred embodiment the analyte polynucleotide standard and internal calibrator coamplify in a single amplification reaction using completely independent primers. This means that no single primer functions to amplify both analyte polynucleotide standard and internal calibrator nucleic acids. In another generally preferred embodiment, at least one primer functions to amplify both analyte polynucleotide standard and internal calibrator nucleic acids in the single amplification reaction. Thus, at least one primer is shared for amplifying the two targets. In yet another generally preferred embodiment, all of the primers participating in the coamplification reaction can be used for amplifying both analyte polynucleotide standard and internal calibrator nucleic acids. In this latter instance, none of the primers are specific for amplifying only one of the two targets (i.e., analyte polynucleotide standard and internal calibrator nucleic acids).

Using the methods disclosed herein, a master calibration curve is first generated by the manufacturer for each lot of reagents, and a set of master calibration curve parameters or coefficients specifying the calibration curve are provided to the end-user. The end-user then performs amplification reactions employing one, or more preferably two adjustment calibrators supplied by the manufacturer, and uses the results of those reactions to correlate the signal of the user's system and the signal of the system that was used by the reagent manufacturer to produce the master curve. When a new reagent lot is first loaded into an end-user's instrument, the master calibration curve parameters or coefficients must be inputted, stored and adjusted before sample results can be reported by the end-user's system.

Notably, there is flexibility in the nature of useful master calibration curves that can be used with the invention. Individual master curves can be created for the amplified analyte polynucleotide and internal calibrator, or a single master curve can be created for the product of a mathematical operation which relates raw data or processed data from two individual master curves for the amplified analyte polynucleotide and internal calibrator. For example, a master calibration curve can be created for the ratio of the time-dependent indicia of amplification for analyte polynucleotide to the time-dependent indicia of amplification for the internal calibrator as a function of the initial amount of analyte polynucleotide standard input into the reaction. Alternatively, separate master calibration curves for analyte polynucleotide and internal calibrator can be adjusted independently using results obtained from coamplification of an adjustment calibrator on an end-user's instrument, and then processed by a mathematical operation to relate the two adjusted curves to each other. This procedure for relating two adjusted curves to each other may involve relating the mathematical equations that describe the independently adjusted curves. Although the equations may be related to each other (e.g., by dividing one equation by the other followed by simplification into a single equation), another approach involves relating to each other (e.g., by division to yield a ratio, or by subtraction to yield a difference) columns of numerical values obtained by solving the individual equations at incremental values of input analyte polynucleotide standard using an electronic spreadsheet. A column of values representing the related results (e.g., processed indicia of amplification) can be used for determining a third equation by standard curve fitting techniques. In all cases, the amount of internal calibrator input into the reactions used for establishing and using master calibration curves preferably is held constant.

Creating a Master Calibration Curve—Independent Adjustment Method

Creating a master calibration curve begins with a step for forming a plurality of standard samples, each containing a constant quantity of a nucleic acid calibrator (i.e., an internal calibrator), and a different known amount of an analyte polynucleotide standard. For example, each of the plurality of standard samples could contain 30,000 copies of the internal calibrator polynucleotide. The different samples could also contain known amounts of the analyte polynucleotide standard, for example, with amounts of the standard differing by 10 fold from one sample to the next.

Next, there is a step for coamplifying in a single amplification reaction the nucleic acid calibrator and the analyte polynucleotide standard, and measuring or otherwise determining indicia of amplification for each of the nucleic acid calibrator and analyte polynucleotide in the standard reactions. Generally speaking, these indicia preferably will be time values required for the amplification reaction to reach a certain point, or for the amount of amplicon produced to have reached a particular amount or threshold value. Such indicia may be measured in cycle numbers for amplification reactions involving thermal or other cycling, or time increments. Indicia representing time increments are preferred for isothermal amplification reactions that do not involve discrete reaction cycles requiring operator or machine intervention to promote the amplification reaction. The result of these procedures is a collection of indicia of amplification for each of the nucleic acid calibrator and analyte polynucleotide as a function of the known starting quantity of analyte polynucleotide standard that was present in the reaction mixture before the amplification reaction was initiated.

Figure 2A:
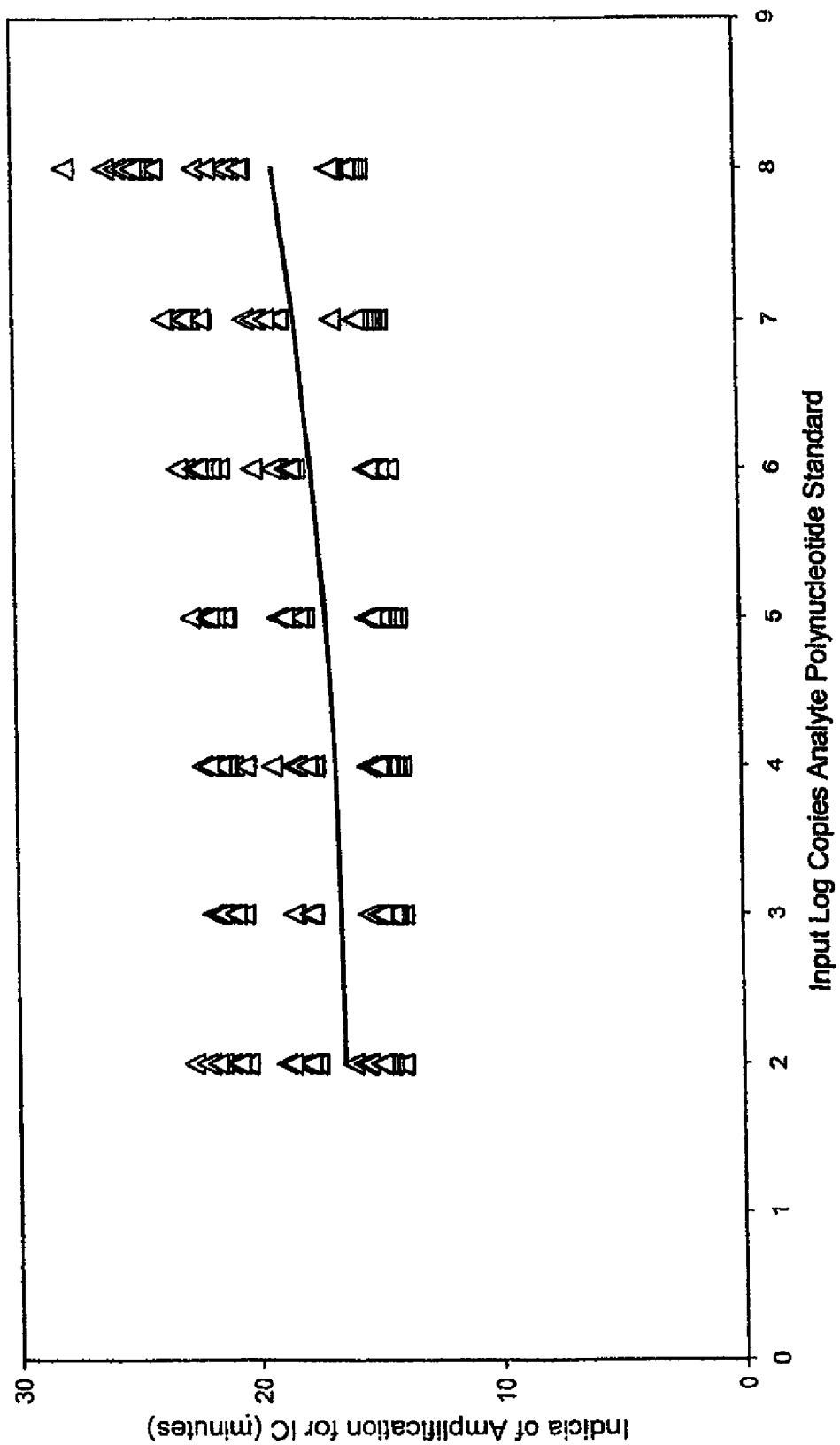
FIGS. 2A-2B are graphs presenting results used for creating master calibration curves.
Figure 2B:
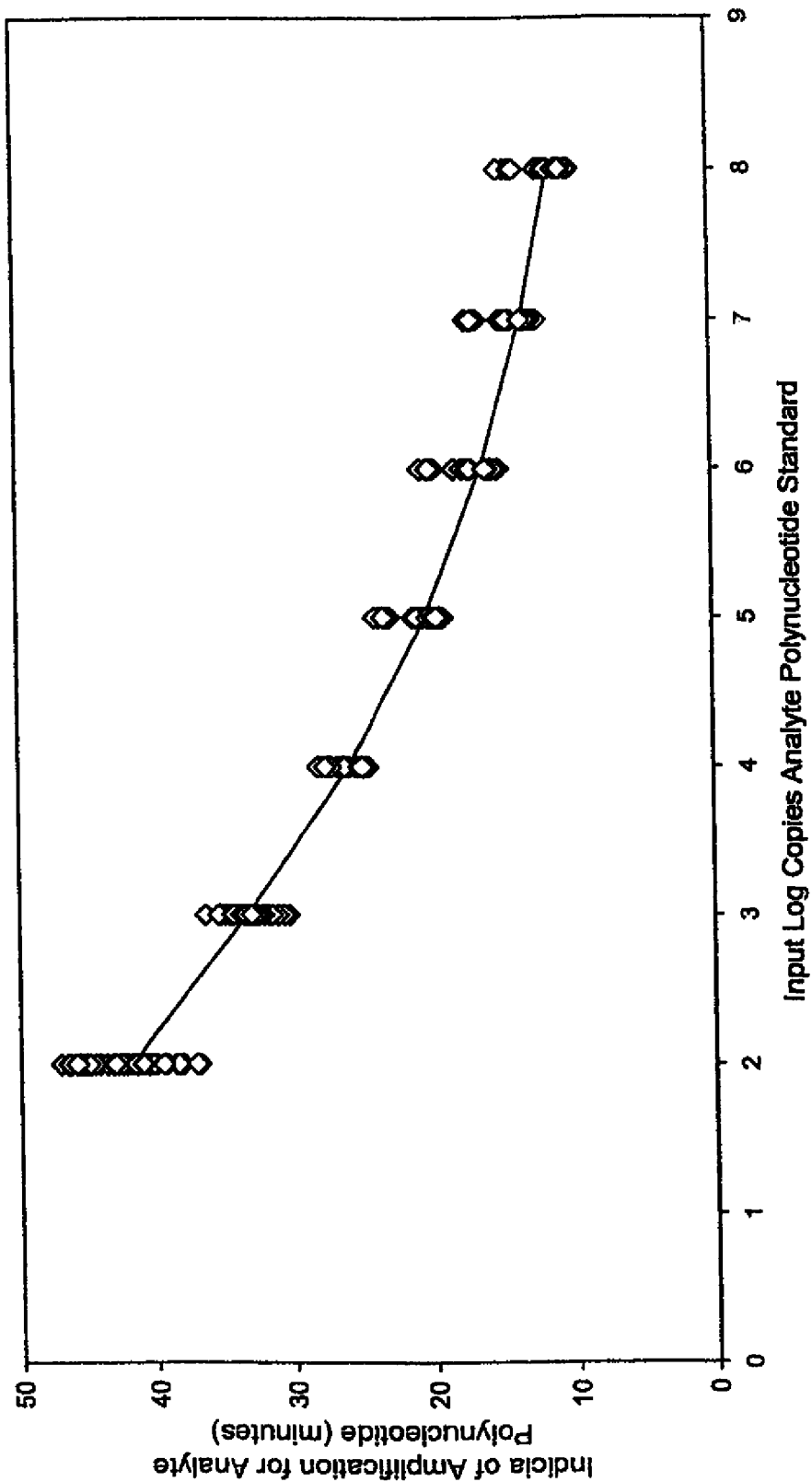

Of course, the resulting indicia of amplification measured for the amplified analyte polynucleotide standard and amplified internal calibrator will be associated with, or related to the amount of analyte polynucleotide standard input into the reaction. This may be formalized by graphing, plotting, or more preferably electronically relating: (a) indicia of amplification for reactions conducted using known amounts of the analyte polynucleotide standard (Tt), and (b) the amount of analyte polynucleotide standard (S) input into the reaction. Likewise, this may involve graphing, plotting, or more preferably electronically relating: (a) indicia of amplification for the internal calibrator (ICt), and (b) the amount of analyte polynucleotide standard (S) input into the reaction. The individual data points in FIGS. 2A-2B represent indicia of amplification measured for the amplified internal calibrator and amplified analyte polynucleotide standard plotted as a function of the amount of analyte polynucleotide standard input into the reaction.

In accordance with the method of creating the calibration curve, the relating procedure or step preferably involves optimizing equations to fit: (1) the indicia of amplification for the amplified analyte polynucleotide standard as a function of the amount of analyte polynucleotide standard input into the reaction, and (2) the indicia of amplification for the amplified internal calibrator as a function of the amount of analyte polynucleotide standard input into the reaction. This can be accomplished by applying standard mathematical curve fitting techniques to each of the data sets to result in equations (i.e., "fitted equations") that define curves associated therewith. Thus, fitted equations for each of two different two-dimensional curves can be obtained by this procedure. In one embodiment, a single type of equation is used for describing each of the curves, with each of the two-dimensional curves being associated with a different set of numerical values for the equation coefficients. The equation used in the curve fitting procedure preferably is a non-linear equation that contains no less than two, more preferably no less than three, and more preferably no less than four coefficients that are optimized or determined during the curve fitting procedure. Some highly preferred equations have exactly four coefficients, while other highly preferred equations have exactly five coefficients. Optimizing an equation to fit the measured indicia of amplification can easily be accomplished using a commercially available software package, such as the SOLVER program which is available as an EXCEL add-in tool for finding an optimal value for a formula, and equation solving from Microsoft Corporation, (Redmond, Wash.). The curves generated by this procedure preferably are shaped such that increasing levels of the analyte polynucleotide standard input into a reaction correlate with reduced indicia of amplification for the analyte polynucleotide standard plot (e.g., the time-of-emergence is reduced), and correlate with increased indicia of amplification for the internal calibrator plot (e.g., the time-of-emergence is increased). Alternatively, the curves generated by this procedure can be shaped such that increasing levels of the analyte polynucleotide standard input into a reaction correlate with reduced indicia of amplification for the analyte polynucleotide standard plot (e.g., the time-of-emergence is reduced), and correlate with substantially constant indicia of amplification for the internal calibrator plot across the range of input analyte polynucleotide standard input into a reaction. The curves drawn in FIGS. 2A-2B represent the graphic products of fitted equations solved over a range of values for the known starting amounts of input analyte polynucleotide standard (S), referred to herein as "fitted indicia of amplification."

Generally speaking, equations useful for preparing and using master calibration curves will contain one, and preferably only one, coefficient that adjusts the baseline without influencing the shape of the curve. This coefficient, referred to herein as a "baseline adjustment coefficient," or a fitted coefficient that adjusts a stored master curve only on an axis specifying the indicia of amplification, affects the position of the curve on the y-axis (i.e., representing the dependent variable) without otherwise affecting the shape of the curve. Although other equations can be used in the curve fitting procedure, the methods described below employed four-parameter logistic equations having the following forms:

$$Tt = y = a_T + b_T / [1 + (S/c_T)^{d_T}] \qquad (\text{Eq 1})$$

$$ICt = y = a_{IC} + b_{IC} / [1 + (S/c_{IC})^{d_{IC}}] \qquad (\text{Eq 2})$$

In these equations, the Tt dependent variable represents the indicia of amplification for a known amount of analyte polynucleotide as a function of the amount of analyte polynucleotide standard (S) used in the reaction, and the ICt dependent variable represents the indicia of amplification for the internal calibrator as a function of the amount of analyte polynucleotide standard (S) used in the reaction. The four coefficients in these equations that can be optimized by standard procedures are identified as $a_n$-$d_n$. The number of copies of analyte polynucleotide input into the amplification reaction is identified as "S" (i.e., the independent variable) in the equations. The $a_n$ coefficient in these equations is the above-discussed baseline adjustment coefficient. Of course, it is to be understood that success in using the present invention does not require the use of any particular equation.

Fitted calibration curves of the type described above, and as illustrated in FIGS. 2A-2B, can serve as master calibration curves, and the solved best-fit equations defining the fitted curves can serve as equations defining the master calibration curves. Simply by providing an end-user with the values of coefficients for an equation defining a master calibration curve permits the end-user to program an analyzer, or data processing component linked thereto, with a manufacturer-provided master curve. When held in a data processing component or computer memory device, the mathematical model of a calibration curve is referred to as a "stored" master calibration curve, or alternatively a "pre-defined" master calibration curve.

Adjusting a Stored Master Calibration Curve

Since no two instruments for performing and monitoring real-time nucleic acid amplification reactions have exactly the same ability to regulate amplification efficiency, and since no two fluorometers give exactly the same signal output for the same level of photon input, the output of each user's system must be adjusted via software to give the same calibrated concentration output as that of the system used to derive the master calibration curve. This adjustment can be accomplished by an end-user performing one, or more preferably two amplification reactions using adjustment calibrators containing known amounts of analyte polynucleotide standard and the same constant amount of internal calibrator as in the reactions used for creating the master calibration curve, determining indicia of amplification for both the analyte polynucleotide standard and internal calibrator, and then adjusting the stored master calibration curve based on these results. When results of the data point(s) from the user-performed reactions are plotted on a graph illustrating the stored master calibration curve, there is expected to be some amount of difference between the user-determined time-dependent indicia of amplification and the time-dependent indicia of amplification predicted from a calculation using the equation defining the stored master calibration curve.

If the end-user employs a single data point obtained from a single adjustment calibrator to adjust the stored master calibration curve, then simply adjusting the stored master calibration curve in the dimension corresponding to indicia of amplification (i.e., the y-axis) to overlay that data point—without otherwise changing the shape of the curve—will be adequate for making the adjustment. This can be accomplished by establishing separate adjustment factors for analyte polynucleotide standard and internal calibrator. In this procedure, the indicia of amplification for the two coamplified targets (i.e., analyte polynucleotide standard and internal calibrator) are first determined. Of course, the starting quantity of analyte polynucleotide standard present in the adjustment calibrator will be known. Next, indicia of amplification values predicted from the stored master curves are calculated by substituting as the independent variable in the respective stored master calibration curve equations the starting quantity of analyte polynucleotide standard present in the adjustment calibrator. The difference calculated by subtracting (a) the value calculated using the master curve equation from (b) the determined indicia of amplification (e.g., these differences being illustrated for two adjustment calibrators in FIG. 3A) can be used as an adjustment factor for modifying the stored master curve equation to result in an equation specifying the adjusted calibration curve. For example, the numerical value of the adjustment factor for internal calibrator can be added to the baseline adjustment coefficient of the stored master curve equation that specifies indicia of amplification for internal calibrator as a function of the starting quantity of analyte polynucleotide standard. Likewise, the numerical value of the adjustment factor for analyte polynucleotide standard can be added to the baseline adjustment coefficient of the stored master curve equation that specifies indicia of amplification for analyte polynucleotide standard as a function of the starting quantity of analyte polynucleotide standard. These modifications to the master curve equations are exemplified in Eq 6. This procedure illustrates how two stored master curves can be independently adjusted using results from a single adjustment calibrator. In a highly preferred embodiment, equations for the independently adjusted calibration curves for internal calibrator and analyte polynucleotide standard, or numerical values calculated therefrom, are related to each other by a mathematical operation (e.g., addition, subtraction, multiplication or division).

Preferably, when using the single-point or other adjustment method there is an additional step for relating fitted equations separately expressing indicia of amplification for analyte polynucleotide standard and internal calibrator, each as a function of the input amount of analyte polynucleotide standard. This may be accomplished, for example, by relating numerical values for (a) indicia of amplification for analyte polynucleotide standard, and (b) indicia of amplification for internal calibrator, each being determined from the adjusted master calibration curves. This may involve a mathematical operation such as multiplication, division, addition or subtraction. For example, there can be calculated the IOA(analyte)/IOA(IC) ratio using the adjusted master calibration curve equations for analyte polynucleotide and internal calibrator at different values of input analyte polynucleotide standard. This preferably involves first calculating the values of the indicia of amplification for analyte polynucleotide standard and the indicia of amplification for internal calibrator at input analyte polynucleotide levels corresponding to the calibration standards used to create the master calibration curve, or by performing the calculation using arbitrary values of input analyte polynucleotide. The product of this operation is a collection of data points representing processed indicia of amplification that are dependent on the amount of analyte polynucleotide input into the amplification reaction. In the particular example discussed herein, the product is a collection of data points representing ratio values that are dependent on the amount of analyte polynucleotide input into the amplification reaction.

If the end-user employs two data points to adjust the stored master calibration curve (i.e., using two different calibration standards), then the following procedure can be used.

Two-Point Adjustment of a Stored Master Calibration Curve

The procedure for adjusting a stored master curve using a two-point adjustment is very similar to the above-described single-point adjustment method. First there are performed two nucleic acid amplification reactions using different adjustment calibrators, each reaction containing different known amounts of the analyte polynucleotide or a fragment thereof (i.e., an analyte polynucleotide standard), together with the same constant amount of nucleic acid calibrator that was used for creating the stored master calibration curve. The adjustment calibrators used in the calibration reactions are referred to as "first" and "second" adjustment calibrators, or alternatively as "Cal_1" and "Cal_2" respectively.

Figure 3A:
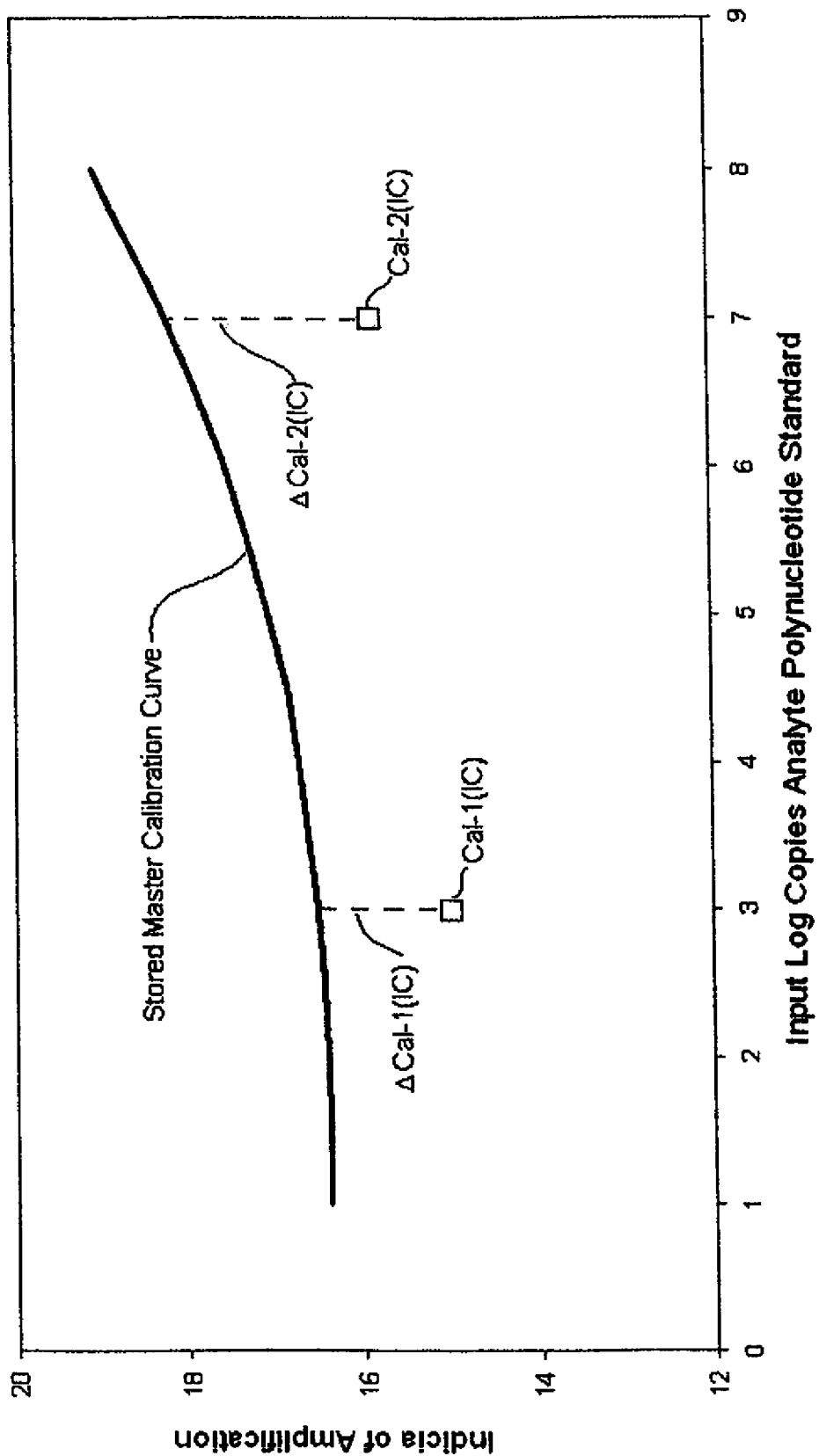
FIGS. 3A-3C are graphs for the best fit curves illustrating indicia of amplification (i.e., y-axis representing TTime values measured in minutes) for the analyte polynucleotide standard and internal calibrator plotted against the log copy level of the analyte polynucleotide contained in a collection of calibration standards (x-axis).
Figure 3B:
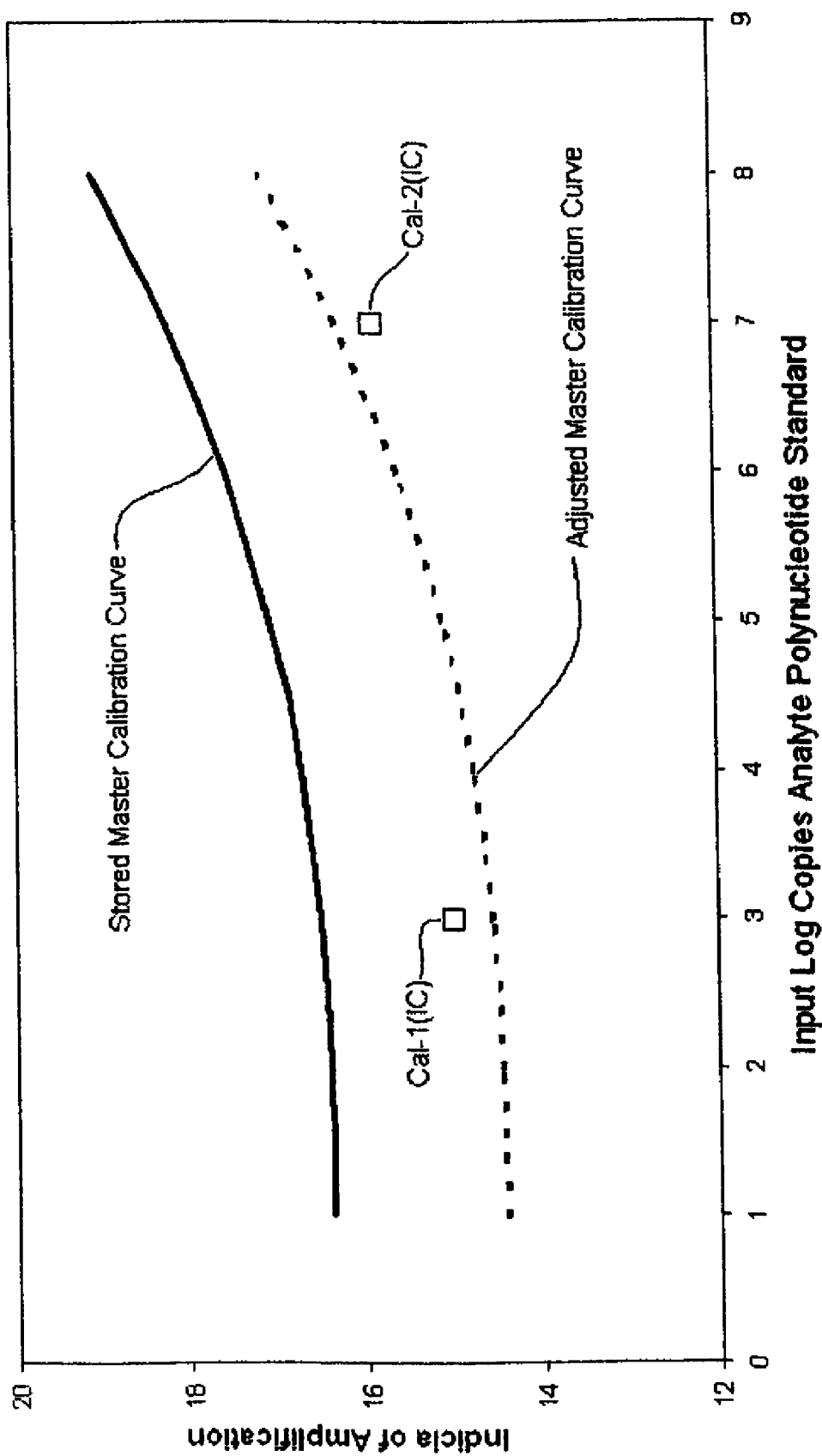
Figure 3C:
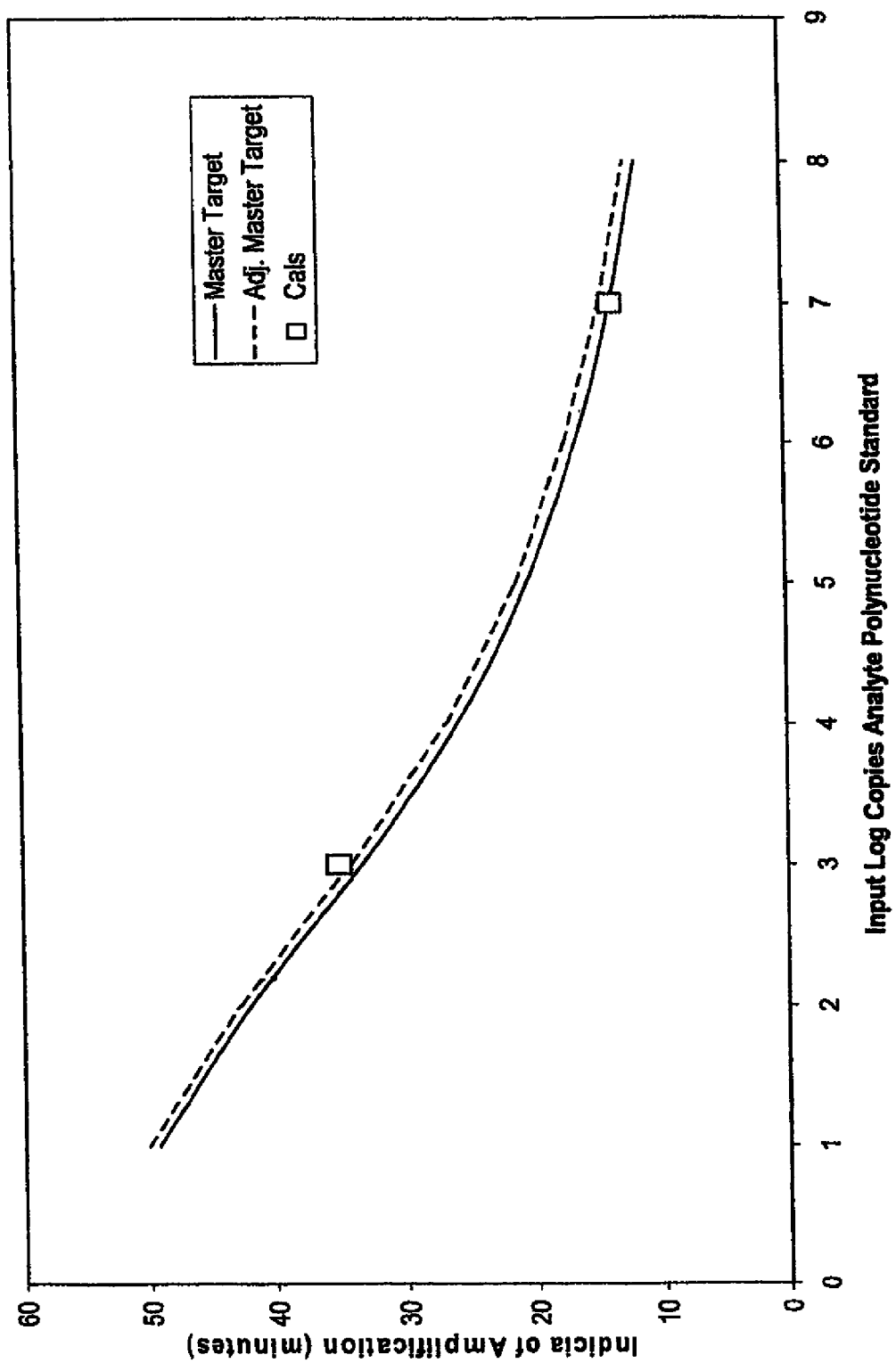

Next, there is determined for each of the two calibration reactions the indicia of amplification for both the internal calibrator (illustrated as data points "Cal_1(IC)" and "Cal_2 (IC)" in FIGS. 3A-313), and the analyte polynucleotide standard (illustrated as data points "Cal_1(analyte)" and "Cal_2 (analyte)" in FIG. 3C).

Next, there is calculated for each of the data points generated from the two calibration reactions the difference between the determined indicia of amplification and the indicia of amplification values from the stored master calibration curve. Preferably, this is done for both the internal calibrator (labeled "$\Delta Cal\_1(IC)$" and "$\Delta Cal\_2(IC)$" in FIGS. 3A-3B), and the analyte polynucleotide (labeled "$\Delta Cal\_1(analyte)$" and "$\Delta Cal\_2(analyte)$" in FIG. 3C). Values for the indicia of amplification falling on the relevant stored master calibration curve can be calculated by solving the equation for the stored master calibration curve using the known amounts of analyte polynucleotide present in each of the two adjustment calibrators, as described above.

Next, there is calculated the average difference between the determined indicia of amplification ("IOA") and the indicia of amplification values from the stored master calibration curve for each curve that is to be adjusted. This can be accomplished using the following equations.

$$\text{Avg}\Delta\text{IOA(analyte)} = [\Delta Cal\_1(\text{analyte}) + \Delta Cal\_2(\text{analyte})]/2 \quad (Eq\ 3)$$

$$\text{Avg}\Delta\text{IOA(IC)} = [\Delta Cal\_1(IC) + \Delta Cal\_2(IC)]/2 \quad (Eq\ 4)$$

Next, there are prepared equations specifying adjusted calibration curves for analyte polynucleotide and internal calibrator. This can be accomplished by adding the calculated values of Avg$\Delta$IOA to the baseline adjustment coefficient (e.g., the coefficient "$a_n$" in the illustrative 4PL equations defining the stored master calibration curves) while maintaining all other coefficients unchanged. This effectively adjusts the stored master calibration curve in only a single dimension (e.g., on the y-axis). By this procedure the stored master calibration curve is adjusted only in the dimension representing the indicia of amplification. Thus, if the equation relating the indicia of amplification (IOA) in the y-dimension as a function of the starting quantity of analyte polynucleotide standard (S) in the x-dimension for a stored master calibration curve is given by $$\text{IOA} = y = a + b/(1 + (S/c)^d), \quad (Eq\ 5)$$

then the equation for the adjusted calibration curve would be $$\text{IOA(adjusted)} = y = (a + \text{Avg}\Delta\text{IOA}) + b/(1 + (S/c)^d). \quad (Eq\ 6)$$

This procedure results in an adjusted calibration curve for analyte polynucleotide standard (i.e., indicia of amplification for analyte polynucleotide standard plotted against input amount of analyte polynucleotide standard), and an adjusted master calibration curve for internal calibrator (i.e., indicia of amplification for internal calibrator plotted against input amount of analyte polynucleotide standard). Graphic plots of stored calibration curves and corresponding adjusted master calibration curves are presented in FIG. 3B (for internal calibrator) and FIG. 3C (for analyte polynucleotide). The Cal_1 and Cal_2 data points used in the procedure also are shown in FIGS. 3B and 3C.

Figure 4:
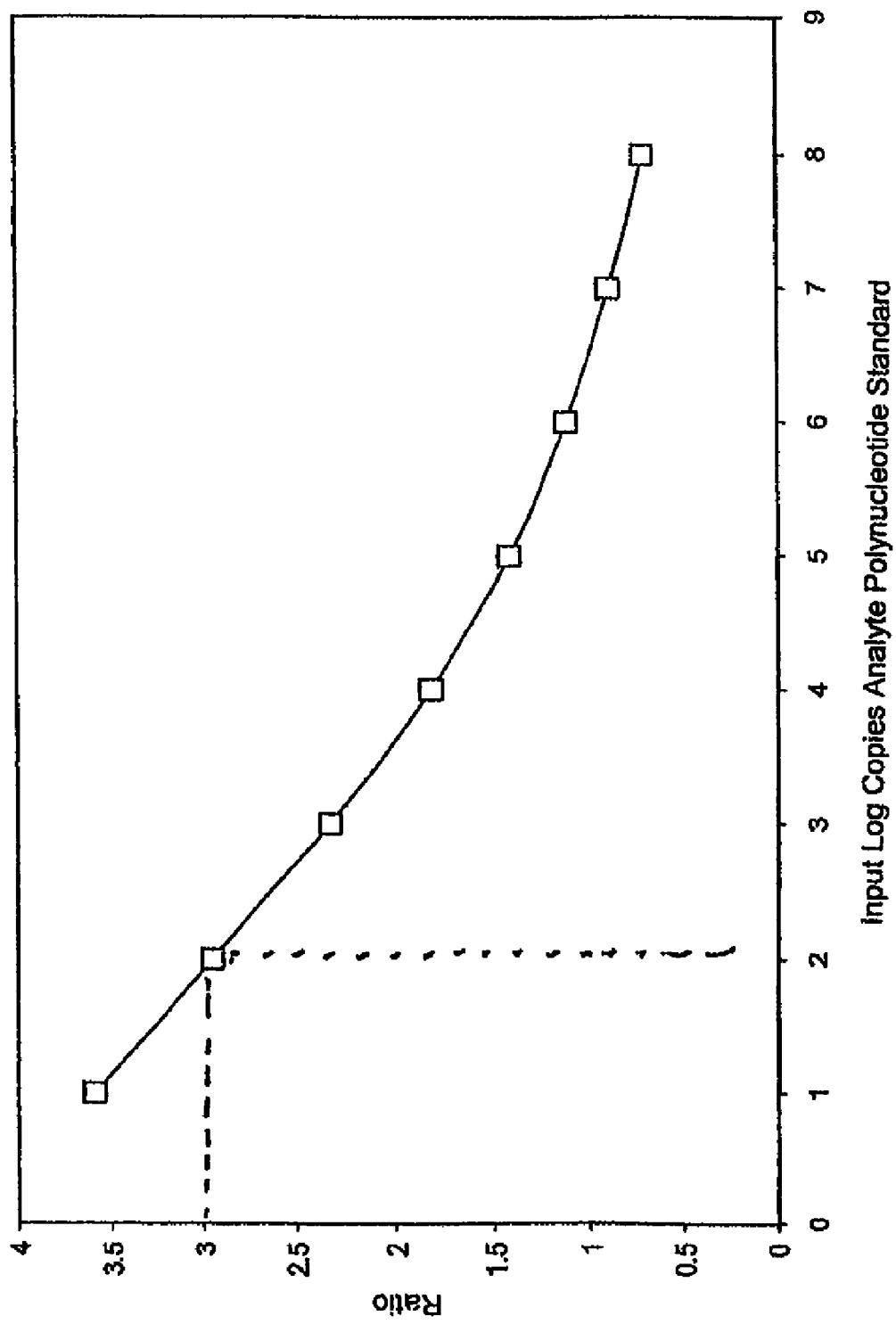
FIG. 4 is a graph illustrating an "IC adjustment plot (ratio) ." Individual data points shown on the graph were calculated at incremental values of the starting amount of analyte polynucleotide standard input into an amplification reaction using results from separate equations for the adjusted master calibration curves shown in FIGS. 2A and 2B. The best-fit curve shown on the graph was determined using a 4PL curve fit.

Preferably, there is an additional step for relating fitted equations separately expressing indicia of amplification for analyte polynucleotide standard and internal calibrator, each as a function of the input amount of analyte polynucleotide standard. This may be accomplished, for example, by relating numerical values for (a) indicia of amplification for analyte polynucleotide standard, and (b) indicia of amplification for internal calibrator, each being determined from the adjusted master calibration curves. This may involve a mathematical operation such as multiplication, division, addition or subtraction. For example, there can be calculated the IOA(analyte)/IOA(IC) ratio using the adjusted master calibration curve equations for analyte polynucleotide and internal calibrator at different values of input analyte polynucleotide standard. This preferably involves first calculating the values of the indicia of amplification for analyte polynucleotide standard and the indicia of amplification for internal calibrator at input analyte polynucleotide levels corresponding to the calibration standards used to create the master calibration curve, or by performing the calculation using arbitrary values of input analyte polynucleotide. The product of this operation is a collection of data points representing processed indicia of amplification that are dependent on the amount of analyte polynucleotide input into the amplification reaction. In the particular example discussed herein, the product is a collection of data points representing ratio values that are dependent on the amount of analyte polynucleotide input into the amplification reaction. FIG. 4 illustrates a plot of these data points.

In preferred embodiments of the single-point and two-point independent adjustment methods, there is yet another step for optimizing an equation, such as a four-parameter logistic (i.e., "4PL") equation, to fit the data points on a plot (e.g., an electronic representation of a two-dimensional plot in a spreadsheet format) of the calculated relationship between the numerical values determined from the adjusted master calibration curves. For example, an equation can be optimized to fit a curve to data points representing the calculated IOA(analyte)/IOA(IC) ratio (i.e., the y-axis) against the amount of input analyte polynucleotide standard (i.e., the x-axis) using conventional curve fitting procedures. Coefficients in the equation can be adjusted using standard software curve fitting techniques to solve for the best-fit curve. An exemplary best-fit curve is shown in FIG. 4. An example equation for the fitted curve could have the following form, and would include numerical solutions for the coefficients $a_{ratio}$-$d_{ratio}$.

$$\text{IOA(analyte)/IOA(IC)} = y_{ratio} = a_{ratio} + b_{ratio}/[1 + (S/c_{ratio})^{d_{ratio}}] \quad (Eq\ 7)$$

In this equation the "$y_{ratio}$" dependent variable is a function of S, which represents the known starting quantity of analyte polynucleotide standard. The fitted curve, which is referred to as an "IC adjustment plot (ratio)," together with the equation describing the fitted curve are both useful for quantifying unknown amounts of analyte polynucleotides in test samples.

Using the Adjusted Master Calibration Curve: Analysis of a Test Sample

An equation defining a master calibration curve, obtained by the procedure described above, can be programmed into, or stored on a processor or machine different from the one(s) used for creating the master calibration curve. Performing an amplification reaction using a test sample containing an unknown amount of analyte polynucleotide and the same amount of internal calibrator polynucleotide, determining particular features of the amplification, and then using those determined features to solve the equation for the stored master calibration curve can provide a numerical output for the amount of analyte polynucleotide present in the test sample.

This can be accomplished using the procedural steps which follow.

First, there is a step for performing an in vitro nucleic acid amplification reaction using a test sample containing an unknown amount of analyte polynucleotide combined in a reaction mixture with the same constant amount of nucleic acid calibrator that was used to create and adjust the master calibration curve. Analyte polynucleotide and nucleic acid calibrator are coamplified in the same amplification reaction, and amplicon synthesis is monitored as a function of time. Using techniques illustrated above, the indicia of amplification for analyte polynucleotide standard and the indicia of amplification for internal calibrator (i.e., the IOA(analyte) and IOA(IC), respectively) are determined for the amplification reaction that included the test sample, and a mathematical operation such as multiplication, division, addition or subtraction is performed to relate the two results to each other. Of course, the nature of the mathematical operation used for processing results from amplification reactions that included a test sample should be the same as the mathematical operation used in the step for relating the independently adjusted stored master curve equations, or numerical values for (a) indicia of amplification for analyte polynucleotide standard, and (b) indicia of amplification for internal calibrator (each being determined from independently adjusted master calibration curves). Exemplary mathematical operations include calculating the IOA(analyte)/IOA(IC) ratio.

Next, using the result of the mathematical operation performed to relate the two results from the test reaction to each other, calculate from the optimized equation fitted to the data points of the calculated relationship between numerical values determined from the adjusted master calibration curves the starting amount of input analyte polynucleotide that must have been present in the reaction mixture. For example, there can be calculated from the equation for the fitted ratio plot (i.e., the IC adjustment plot (ratio)) the amount of input analyte polynucleotide (i.e., "S" in Eq 7) that must have been present in the reaction mixture using the calculated ratio of IOA(analyte)/IOA(IC) (i.e., "$Y_{ratio}$" in Eq 7) for the test sample. FIG. 4 graphically illustrates how the IC adjustment plot (ratio) and the calculated IOA(analyte)/IOA(IC) ratio for a test sample (shown as being about 3.0) can be used to determine the amount of analyte polynucleotide (shown as being about 2 log copies) in the test sample.

The foregoing illustrates the invention by relating as a ratio results from the independently adjusted master calibration curves for (a) indicia of amplification for the analyte polynucleotide standard as a function of the known starting quantity of analyte polynucleotide standard, and (b) indicia of amplification for the internal calibrator as a function of the known starting quantity of analyte polynucleotide standard. However, excellent results also have been achieved by relating results from the independently adjusted master calibration curves as a difference (i.e., using subtraction instead of division to carry out the mathematical relating step). In this latter case, the indicia of amplification for the analyte polynucleotide and internal calibrator determined for the test sample are similarly related to each other by subtraction to determine a difference value. That difference value is then compared to the difference-based adjusted calibration curve to determine the starting quantity of analyte polynucleotide present in the test sample. Relating independently adjusted master calibration curves by addition and multiplication also are contemplated as alternative approaches to be used with the quantitation methods detailed herein.

Creating a Master Calibration Curve Based on Preliminary Processing of Results for Indicia of Amplification The preceding sections described independent adjustments to master curves for indicia of amplification for analyte polynucleotide and coamplified nucleic acid calibrator, followed by use of the separately adjusted curves in a procedure involving a mathematical operation employing results from the separately adjusted curves. This procedure is referred to as the "independent adjustment" method. In a particular instance discussed above, results from the separately adjusted master curves were used to calculate the IOA(analyte)/IOA(IC) ratio.

Following is a description of an alternative method wherein a mathematical operation is first performed using unadjusted data, and the result then used to create a master curve. To simplify the comparison, the following description concerns preparation of a master curve that relates results from amplification of analyte polynucleotide standard and nucleic acid calibrator as a ratio. However, it is to be understood that indicia of amplification for the analyte polynucleotide and nucleic acid calibrator can be related to each other by any mathematical function such as multiplication, division, addition or subtraction, prior to use for creating a processed indicia master calibration curve.

As before, the procedure for creating a master calibration curve begins with a step for forming a plurality of standard samples, each containing a constant quantity of a nucleic acid calibrator (i.e., an internal calibrator), and a different known amount of an analyte polynucleotide standard.

Next, there is a step for coamplifying in a single amplification reaction the nucleic acid calibrator and the analyte polynucleotide standard, and measuring or otherwise determining indicia of amplification for each of the internal calibrator and analyte polynucleotide standard in the reactions. Again as before, the result of these procedures is a collection of indicia of amplification for each of the nucleic acid calibrator and analyte polynucleotide standard as a function of the known starting quantity of analyte polynucleotide standard that was present in the reaction mixture before the amplification reaction was initiated.

Next, the collection of indicia of amplification for each of the nucleic acid calibrator and analyte polynucleotide as a function of the known starting quantity of analyte polynucleotide standard from individual amplification reactions are used to perform a mathematical function, such as division to establish a ratio, or subtraction to establish a difference. Continuing with the example from above, the numerical value for the indicia of amplification for analyte polynucleotide measured for a particular level of input analyte polynucleotide standard can be divided by the numerical value for the indicia of amplification for nucleic acid calibrator measured in the same amplification reaction. The result of this procedure is a collection of data points representing calculated ratios as a function of the known starting quantity of analyte polynucleotide standard that was present in the reaction mixture before the amplification reaction was initiated. Notably, in this instance the mathematical operation that relates the indicia of amplification for analyte polynucleotide standard and internal calibrator is performed prior to any adjustment of the calibration curves using results from an adjustment calibrator. This contrasts with the approach used for conducting the independent adjustment method.

In accordance with the method of creating the master calibration curve based on preliminary processing of results for indicia of amplification, an equation is optimized to fit the processed indicia of amplification for the amplified analyte polynucleotide standard and nucleic acid calibrator as a function of the amount of analyte polynucleotide standard input into the reaction. Again, this can be accomplished by applying standard mathematical curve fitting techniques to the data set to result in an equation (i.e., a "fitted equation") that defines a curve associated therewith. Thus, an equation for the best-fit curve can be obtained by this procedure. Any equation that would be appropriate for use in curve fitting the individual indicia of amplification (i.e., treating analyte polynucleotide standard and nucleic acid calibrator independently) also would be useful for establishing an equation that defines a curve for the processed indicia of amplification. For example, the equation used for demonstrating the master curve adjustment method had the following form.

$$P = a_p + b_p[1 + (S/c_p)^{d_p}] \quad \text{(Eq 8)}$$

Figure 5:
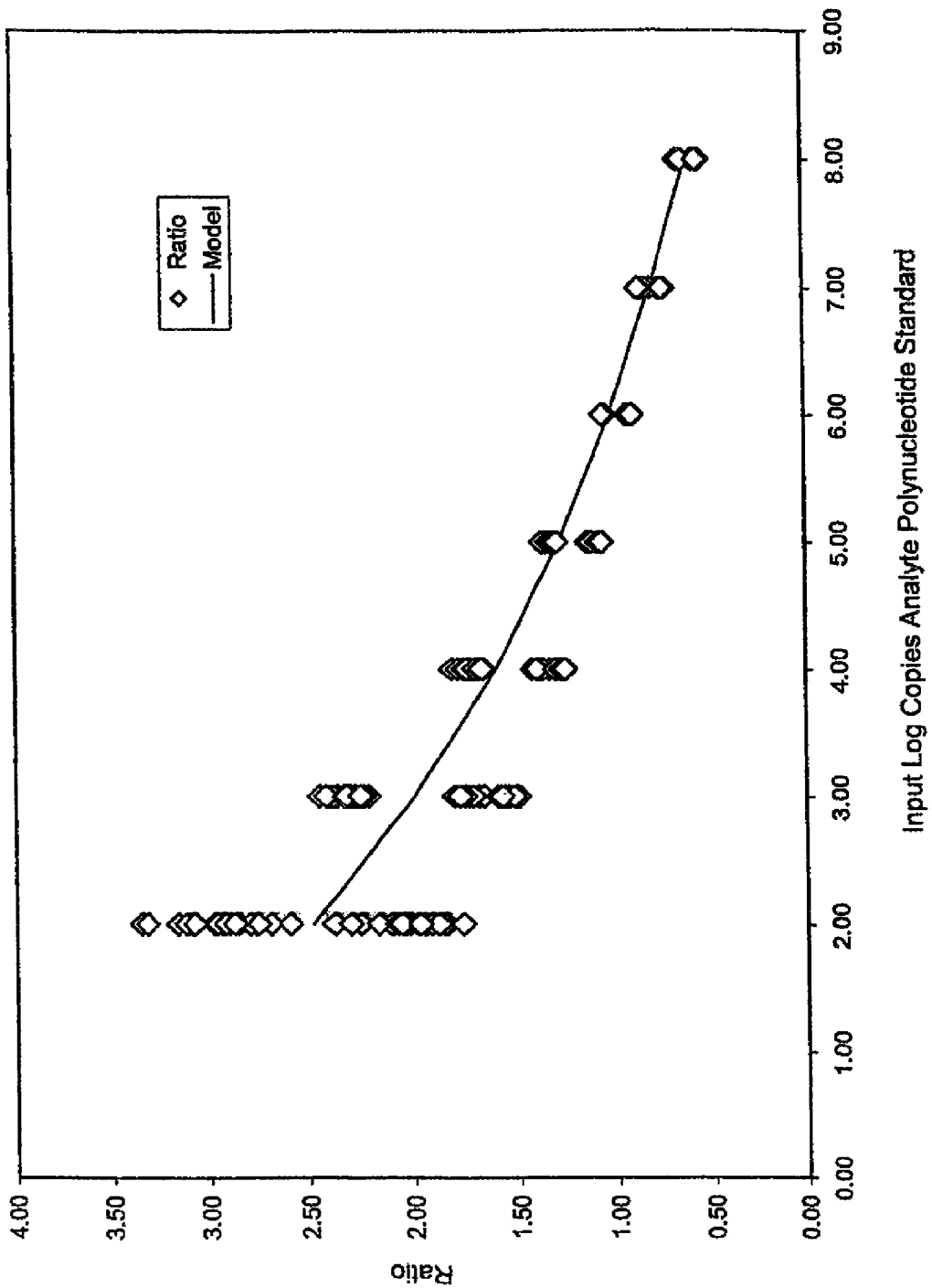
FIG. 5 is a graphic plot showing data points representing ratios for IOA(analyte)/IOA(IC) calculated from raw data. Also shown is a curve fitted to the collection of data points.

In this equation, the dependent variable (P) represents the value of the processed indicia of amplification for a known amount of analyte polynucleotide as a function of the amount of analyte polynucleotide (S) used in the reaction. The four coefficients that can be optimized by standard procedures are identified as $a_p$-$d_p$. The number of copies of analyte polynucleotide input into the amplification reaction is identified by "S" (i.e., the independent variable) in the equations. The coefficient $a_p$ in the equation is the above-discussed baseline adjustment coefficient. FIG. 5 illustrates a collection of data points representing calculated ratios as a function of the known starting quantity of analyte polynucleotide standard that was present in the reaction mixture before the amplification reaction was initiated. Also illustrated in FIG. 5 is a curve, specified by an optimized equation, fitted to the collection of data points.

Adjusting a Stored Processed Indicia Master Calibration Curve

The procedure for adjusting a master calibration curve based on preliminary processing of results for indicia of amplification is substantially similar to the procedure used for adjusting independent calibration curves. More specifically, amplification reactions are performed using one or two adjustment calibrators, and indicia of amplification for the analyte polynucleotide and nucleic acid calibrator are determined. The resulting indicia of amplification for the two targets are then related to each other by the same mathematical operation that was used for creating the processed indicia master calibration curve. For example, if the processed indicia calibration curve was created using a ratio of indicia of amplification for analyte polynucleotide and nucleic acid calibrator plotted against the known starting quantities of analyte polynucleotide standard used in the reactions, then the indicia of amplification measured for the calibration standard would be related to each other as a ratio in the same manner. Alternatively, if the processed indicia calibration curve was created using the difference between the indicia of amplification for analyte polynucleotide and nucleic acid calibrator plotted against the known starting quantities of analyte polynucleotide standard used in the reactions, then the indicia of amplification determined for the adjustment calibrator would similarly be related to each other by subtraction. If a one point adjustment of the master calibration curve is to be performed, then it is only necessary to adjust the curve to overlay the calibration standard data point (i.e., representing the ratio of indicia of amplification for analyte polynucleotide and nucleic acid calibrator) in the dimension corresponding to the processed indicia, and not in the dimension corresponding to the known starting quantities of analyte polynucleotide standard used in the reactions. This can be accomplished by calculating the difference between the calibration standard data point and the stored master curve in the dimension corresponding to processed indicia, and then adjusting the curve using that average difference according to the procedure described above. Similarly, a two point adjustment of a stored processed indicia master calibration curve would be carried out by calculating the average difference between the fitted curve and the calibration standard data points in the dimension corresponding to the processed indicia of amplification, and then adjusting the curve using that average difference essentially according to the procedure described above.

The adjusted processed indicia master calibration curve is useful for estimating the amount of analyte polynucleotide contained in a test sample using the indicia of amplification measured in an amplification reaction. As before, there is a step for performing an in vitro nucleic acid amplification reaction using the test sample containing an unknown amount of analyte polynucleotide combined in a reaction mixture with the same constant amount of nucleic acid calibrator that was used to create the master calibration curve. Analyte polynucleotide and nucleic acid calibrator are amplified in the same amplification reaction, and amplicon synthesis is monitored as a function of time. Using techniques illustrated above, the IOA(analyte) and IOA(IC) are determined for the test sample, and a mathematical operation such as multiplication, division, addition or subtraction is performed to relate the two results to each other. Exemplary mathematical operations include calculating the IOA(analyte)/IOA(IC) ratio. The result of this calculation can then be compared with the adjusted processed indicia master calibration curve to estimate the initial amount of analyte polynucleotide contained in the test sample.

Useful Amplification Methods

Examples of amplification methods useful in connection with the present invention include, but are not limited to: Transcription Mediated Amplification (TMA), Single-Primer Nucleic Acid Amplification, Nucleic Acid Sequence-Based Amplification (NASBA), the Polymerase Chain Reaction (PCR), Strand Displacement Amplification (SDA), Self-Sustained Sequence Replication (3SR), DNA Ligase Chain Reaction (LCR) and amplification methods using self-replicating polynucleotide molecules and replication enzymes such as MDV-1 RNA and Q-beta enzyme. Methods for carrying out these various amplification techniques respectively can be found in U.S. Pat. No. 5,399,491, U.S. patent application Ser. No. 11/213,519, published European patent application EP 0 525 882, U.S. Pat. No. 4,965,188, U.S. Pat. No. 5,455,166, Guatelli et al., *Proc. Natl. Acad. Sci. USA* 87:1874-1878 (1990), International Publication No. WO 89/09835, U.S. Pat. No. 5,472,840 and Lizardi et al., *Trends Biotechnol.* 9:53-58 (1991). The disclosures of these documents which describe how to perform nucleic acid amplification reactions are hereby incorporated by reference.

Amplification reactions that require only a single extendable primer are particularly preferred for use in connection with the disclosed algorithm. These reactions include transcription-associated amplification systems that employ a single extendable primer in combination with a 3'-blocked oligonucleotide that cannot be extended by a nucleic acid polymerase. Methods for carrying out such amplification reactions are, for example, detailed in U.S. patent application Ser. No. 11/213,519.

Examples of Useful Indicia of Amplification

A variety of indicia of amplification can be used in connection with the disclosed method. For example, mathematical and computing techniques that will be familiar to those having an ordinary level of skill in the art can be used to identify the time of occurrence of the maximum of the first derivative, or the time of occurrence of the maximum of the second derivative of a real-time run curve. Approaches for determining these features of a growth curve have been detailed by Wittwer et al., in U.S. Pat. No. 6,503,720, the disclosure of which is incorporated by reference herein. Other useful approaches involve calculating a derivative of a growth curve, identifying a characteristic of the growth curve, and then determining the threshold time or cycle number corresponding to the characteristic of the derivative. Such techniques have been disclosed in U.S. Pat. No. 6,783,934, the disclosure of which is incorporated by reference. Still other useful indicia of amplification include "TTime" and "TArc." Notably, different approaches for determining TArc values employ directionally similar vectors (i.e., resulting in a value identified simply by "TArc"), and directionally opposed vectors (i.e., resulting in a value identified as "OTArc"). General descriptions of these methods latter are given below.

Methods of Determining TTime Values

Simply stated, TTime values estimate the time at which a particular threshold indicating amplicon production is passed in a real-time amplification reaction. The algorithm for calculating and using TTime values has been described in the U.S. patent application identified by Ser. No. 60/659,874, the disclosure of which is incorporated by reference. According to this algorithm, a curve fit procedure is applied to normalized and background-adjusted data. Although any of the well-known curve fit methodologies may be employed, in a preferred embodiment, a linear least squares ("LLS") curve fit is employed. The curve fit is performed for only a portion of the data between a predetermined low bound and high bound. The ultimate goal, after finding the curve which fits the data, is to estimate the time corresponding to the point at which the curve or a projection thereof intersects a predefined threshold value. In one embodiment, the threshold for normalized data is 0.11. The high and low bounds are determined empirically as that range over which curves fit to a variety of control data sets exhibit the least variability in the time associated with the given threshold value. In one embodiment, the low bound is 0.04 and the high bound is 0.36. The curve is fit for data extending from the first data point below the low bound through the first data point past the high bound. Next, there is made a determination whether the slope of the fit is statistically significant. For example, if the p value of the first order coefficient is less than 0.05, the fit is considered significant, and processing continues. If not, processing stops. Alternatively, the validity of the data can be determined by the $R^2$ value. The slope m and intercept b of the linear curve y=mx+b are determined for the fitted curve. With that information, TTime can be determined as follows:

$$TTime=(Threshold-b)/m \qquad (Eq\ 9)$$

Methods of Determining TArc Values

Time-dependent indicia of amplification referred to as "TArc" and "OTArc" are determined using vector-based analyses of real-time run curves. The TArc value identifies the point in time at which a growth curve begins to curve or "inflect" upward. This determined point can be used for creating a standard curve, or for establishing a parameter of an amplification reaction that relates to the amount or concentration of an analyte polynucleotide in a test sample. The vector analysis is most conveniently carried out using growth curves having data points distributed over substantially uniform time intervals. Detailed presentations concerning the determination and use of TArc and OTArc values appear in the U.S. patent application having Ser. No. 60/693,455, the specification and drawings of this application being incorporated by reference herein.

Alternative Equations for Performing the Curve Step of the Master Curve Adjustment Method Notably, although 4-parameter logistic (4PL) equations were used particularly for illustrating the invention, other mathematical functions can also be used in the procedure. Indeed, substantially any equation having a baseline adjustment coefficient may be used in the curve fitting procedure to model real-time amplification results. As indicated above, the baseline adjustment coefficient serves the purpose of adjusting the full curve only in a vertical dimension on a standard plot, without changing the shape of the curve.

Those having an ordinary level of skill in the art will appreciate that numerous types of equations may be used in the procedures disclosed herein. Transition functions containing baseline coefficients can be used to model real-time data, specifically indicia of amplification, and create master calibration curves having a baseline coefficient that can be modified in the master calibration curve adjustment procedure. Examples of symmetric transition functions include, but are not limited to: Sigmoid, Gaussian Cumulative, Lorentzian Cumulative and Cumulative Symmetric Double Sigmoidal. Examples of asymmetric transition functions include, but are not limited to: Logistic Dose Response (LDR), Log Normal Cumulative, Extreme Value Cumulative, Pulse Cumulative, Pulse Cumulative with Power Term, Weibull Cumulative, Asymmetric Sigmoid, Asymmetric Sigmoid Reverse Asymmetry, Cascade Formation, and Cumulative Exponentially Modified Gaussian. Additionally, simple linear and non-linear equations, such as multiple order polynomials, power, exponential and logarithmic functions can be used to model real-time data with subsequent adjustment of the baseline coefficient, as detailed herein. Kinetic functions with baseline coefficients can also be used in the same manner. Exemplary basic kinetic equations containing baseline coefficients include but are not limited to: Half Order Decay and Formation, First Order Decay and Formation, Second Order Decay and Formation, Second Order Decay and Formation (Hyperbolic Forms), and Third Order Decay and Formation, Variable Order Decay and Formation. Exemplary complex kinetic equations containing baseline coefficients include but are not limited to: Simultaneous First and Second Order Decay and Formation, First Order Sequential Formation, Two Component First Order Decay, Two First Order Independent Decay and Formation, Two Second Order Independent Decay and Formation, and First and Second Order Independent Decay and Formation. Exemplary kinetic equilibrium equations containing baseline coefficients include but are not limited to: Simple Equilibrium (Forward and Reverse Rate), Simple Equilibrium (Net Rate and Equilibrium Concentration), Complex Equilibrium A=B+C, and Complex Equilibrium A+B=C+D. Exemplary intermediate kinetic equations containing baseline coefficients include but are not limited to: First Order Intermediate and First Order Intermediate with Equilibrium. One of ordinary skill in the art will readily understand that success of the disclosed master calibration curve adjustment method does not depend on the use of any particular equation for performing the curve fitting step leading to creation of a master calibration curve. Indeed, it is believed that any equation having coefficients that can be optimized in a curve fitting procedure, and that contains a baseline adjustment coefficient can be used for performing the disclosed master calibration curve adjustment procedures.

All of the above-listed equation types have been used for curve fitting indicia of amplification for real-time data with excellent results, as judged by the goodness of fit. Accordingly, each of the equation types can be used to carry out the disclosed methods (e.g., independent adjustment methods) with excellent results. This is because success of the procedure depends not on the particular equation used, but on its ability to fit the data optimally. Moreover, use of different equation types within a single master curve adjustment procedure is within the scope of the invention. This means that indicia of amplification for analyte polynucleotide standard as a function of the quantity of analyte polynucleotide standard input into the amplification reaction can be modeled by one type of equation, and indicia of amplification for internal calibrator as a function of the quantity of analyte polynucleotide standard input into the amplification reaction can be modeled by a second type of equation in the procedure. As well, the result of the process of mathematically relating one curve (or the equation specifying that curve) to another (or the equation specifying that curve) can be modeled by yet a third type of equation.

Apparatus for Implementing the Calibration Algorithm

The methods disclosed herein are conveniently implemented using a computer or similar processing device ("computer" hereafter). In different preferred embodiments, software or machine-executable instructions for performing an algorithm can be loaded or otherwise held in a memory component of a freestanding computer, or in a memory component of a computer linked to a device used for monitoring, preferably as a function of time, the amount of an a product undergoing analysis. In a highly preferred embodiment, software for executing the calibration algorithm is held in a memory component of a computer that is linked to, or that is an integral part of a device capable of monitoring the amount of an amplicon present in a reaction mixture as a function of time.

Indeed, either or both of a controller system for controlling a real-time amplification device and/or the detection system of the real-time amplification device can be coupled to an appropriately programmed computer which functions to instruct the operation of these instruments in accordance with preprogrammed or user input instructions. The computer preferably also can receive data and information from these instruments, and interpret, manipulate and report this information to the user.

In general, the computer typically includes appropriate software for receiving user instructions, either in the form of user input into a set of parameter fields, or in the form of preprogrammed instructions (e.g., preprogrammed for a variety of different specific operations). The software then converts these instructions to appropriate language for instructing the operation of the real-time amplification controller to carry out the desired operation. The computer also is capable of receiving data from the one or more sensors/detectors included within the system, and interprets the data in accordance with the programming. The system preferably includes software that correlates a feature of a growth curve representing the quantity of amplified copies of the nucleic acid of interest as a function of time, as detected by the detector, to the number of copies of the nucleic acid of interest present in a test sample.

Preferably, when the computer used for executing the disclosed calibration algorithm is an integral component of an apparatus for performing and analyzing real-time nucleic acid amplification reactions, the apparatus preferably comprises a temperature-controlled incubator, a detection device for collecting signals, an analyzing device (e.g., a computer or processor) for analyzing signals and an output device for displaying data obtained or generated by the analyzing device. The analyzing device may be connected to the temperature-controlled incubator through an input device known in the art, and/or connected to an output device known in the art for data display. In one embodiment, the temperature-controlled incubator is capable of temperature cycling.

Generally speaking, the various components of an apparatus for performing the real-time nucleic acid amplification useful in connection with the disclosed methods will be conventional components that will be familiar to those having an ordinary level of skill in the art. The temperature-controlled incubator used to perform and analyze real-time nucleic acid amplification may be of a conventional design which can hold a plurality of reaction tubes, or reaction samples in a temperature-controlled block in standard amplification reaction tubes or in wells of a multiwell plate. In one aspect, the detection system is suitable for detecting optical signals from one or more fluorescent labels. The output of the detection system (e.g., signals corresponding to those generated during the amplification reaction) can be fed to the computer for data storage and manipulation. In one embodiment, the system detects multiple different types of optical signals, such as multiple different types of fluorescent labels and has the capabilities of a microplate fluorescence reader. The detection system is preferably a multiplexed fluorimeter containing an excitation light source, which may be a visible light laser or an ultraviolet lamp or a halogen lamp, a multiplexer device for distributing the excitation light to the individual reaction tubes and for receiving fluorescent light from the reaction tubes, a filtering means for separating the fluorescence light from the excitation light by their wavelengths, and a detection means for measuring the fluorescence light intensity. Preferably, the detection system of the temperature-controlled incubator provides a broad detection range that allows flexibility of fluorophore choice, high sensitivity and excellent signal-to-noise ratio. Optical signals received by the detection system are generally converted into signals which can be operated on by the processor to provide data which can be viewed by a user on a display of a user device in communication with the processor. The user device may comprise a user interface or may be a conventional commercially available computer system with a keyboard and video monitor. Examples of data which can be displayed by the user device include amplification plots, scatter plots, sample value screens for all the tubes or reaction vessels in the assembly and for all labels used, an optical signal intensity screen (e.g., fluorescent signal intensity screen), final call results, text reports, and the like.

Comparison of Different Master Calibration Curve Adjustment Methods

Illustrated below is a comparison of two different approaches for adjusting master calibration curves by the methods described above. In each case, master calibration curves were prepared using results obtained on a first set of amplification/detection instruments (i.e., simulating production of master curves by an assay manufacturer). The prepared master curve(s) were then used for analyzing results obtained on a different amplification detection instrument (i.e., simulating an instrument operated by end-user or customer).

In the first approach, results for indicia of amplification for analyte polynucleotide standard were divided by indicia of amplification for internal calibrator to calculate a ratio. Curve fitting was carried out to optimize coefficients of an illustrative 4PL equation to describe ratio values as a function of the starting quantity of analyte polynucleotide standard used in the amplification reactions. This single master calibration curve, termed a "processed indicia master calibration curve," was then adjusted using results obtained by amplification of either one or two adjustment calibrators on the simulated end-user instrument. Importantly, results obtained by adjustment of the processed indicia master calibration curve were compared to a complete calibration curve produced on the simulated end-user instrument (i.e., a "local" calibration curve), which represented the gold standard calibration curve.

In the second approach, two master calibration curves (i.e., one for indicia of amplification for analyte polynucleotide standard as a function of the starting quantity of analyte polynucleotide standard, and a second for indicia of amplification for internal calibrator as a function of the starting quantity of analyte polynucleotide standard) were prepared by curve fitting to optimize coefficients of the illustrative 4PL equation using results obtained on the simulated manufacturer instruments. The two curves were then independently adjusted using results obtained by amplification of either one or two adjustment calibrators on the simulated end-user instrument. Equations defining the independently adjusted calibration curves were then related to each other by a mathematical operation. In the Example, the equation defining the adjusted curve for analyte polynucleotide standard was divided by the equation for internal calibrator to yield an equation for the independently adjusted calibration curve (i.e., again relating two equations by a process of division to yield a ratio). As in the first approach, results obtained using the independently adjusted calibration curve were compared to a complete calibration curve produced on the simulated end-user instrument (i.e., a "local" calibration curve), which again represented the gold standard calibration curve.

An isothermal single-primer transcription-associated amplification system was used in the following Example to demonstrate the master calibration curve adjustment method. The analyte polynucleotide standard used in the procedure was a model viral polynucleotide. Oligonucleotides (i.e., primers) used for amplifying the analyte polynucleotide standard and the unrelated internal calibrator in the coamplification reaction were fully independent, meaning the two amplification reactions occurring in a single reaction vessel did not share primers in the individual amplification reactions. Moreover, the two amplicons had different lengths and different % G+C contents. The fact that excellent results were obtained under these stringent assay conditions indicated that excellent results also can be expected using one or more primers that amplify both nucleic acid targets, as well as using an internal calibrator giving rise to amplicons having a length and % G+C content that is the same as the analyte polynucleotide standard.

Notably, the quantitative real-time results described in the following Example correspond to subsets of the data presented in FIGS. 1, 2A-2B, and 5. More specifically, these figures present aggregated results obtained when single-primer amplification reactions were performed and monitored on four different amplification/detection instruments (i.e., instruments 1-4). In the following demonstration, instrument 1 served as the model end-user instrument. Thus, the end-user data described below, for example in connection with the local calibration curve(s), corresponds to the subset of data points appearing in FIGS. 2A-2B and 5 that were obtained using only instrument 1. Instruments 2-4 modeled instruments that could be used for preparing master calibration curves that were useful for analyzing data obtained on a different instrument. Thus, results used for creating the below-referenced master calibration curves represented the subset of data points appearing in FIGS. 2A-2B and 5 that were obtained using only instruments 2-4. Of course, the preparation, adjustment and use of master calibration curves by the methods disclosed herein using only a single nucleic acid amplification/detection instrument also fall within the scope of the invention.

Example 1

Preparation and Use of Stored Master Calibration Curves

A collection of standard samples were first prepared for standard single-primer isothermal nucleic acid amplification reactions that were conducted in accordance with the general method disclosed in published U.S. Patent Application No. 2006/0046265A1. Samples contained a range of starting quantities of an analyte polynucleotide standard that spanned from $10^2$-$10^8$ copies/sample. Each sample additionally included a constant starting quantity of 30,000 copies of an internal calibrator nucleic acid that was unrelated to the analyte polynucleotide standard. In this instance the internal calibrator was an artificial target sequence consisting of a scrambled sequence of bases represented in a length of HIV-1 nucleic acid (i.e., a viral target different from the analyte polynucleotide standard) that was different from the length of the sequence to be amplified in the analyte polynucleotide standard. Thus, internal calibrator and analyte polynucleotide standard amplicons synthesized in the amplification reactions differed in both length and % G+C content. Additionally, the analyte polynucleotide standard and internal calibrator coamplified in the nucleic acid amplification reactions using different oligonucleotides (i.e., the two targets did not amplify using any shared primer).

Time-dependent synthesis of analyte polynucleotide standard and internal calibrator amplicons was assessed by monitoring fluorescent emissions of two amplicon-specific molecular torch hybridization probes. Real-time growth curves were analyzed using the threshold-based TTime algorithm for determining indicia of amplification for each of the analyte polynucleotide standard and internal calibrator amplicons. Since starting quantities of the analyte polynucleotide standard were known for each reaction, the results of the analysis yielded (a) indicia of amplification for the analyte polynucleotide standard as a function of the starting quantity of the analyte polynucleotide standard, and (b) indicia of amplification for internal calibrator as a function of the starting quantity of the analyte polynucleotide standard. Results were used for preparing three different master calibration curves.

A local calibration curve was prepared using results obtained on a model end-user amplification/detection instrument that was not used for preparing the master calibration curves. Briefly, a full collection of standard samples as described above (i.e., containing analyte polynucleotide standard and internal calibrator) was used to create a calibration curve that relates indicia of amplification for analyte polynucleotide to indicia of amplification for internal calibrator as a ratio. This local curve is the result expected for quantitation carried out on an end-user instrument, and so represents a gold standard that is the objective of the adjustment procedure. The local calibration curve is presented in FIGS. 9-12 as the heavy dotted line. Filled diamonds on each of the graphs indicate replicate results used for creating the local curve, again by standard curve techniques to optimize a 4PL equation.

Figure 6:
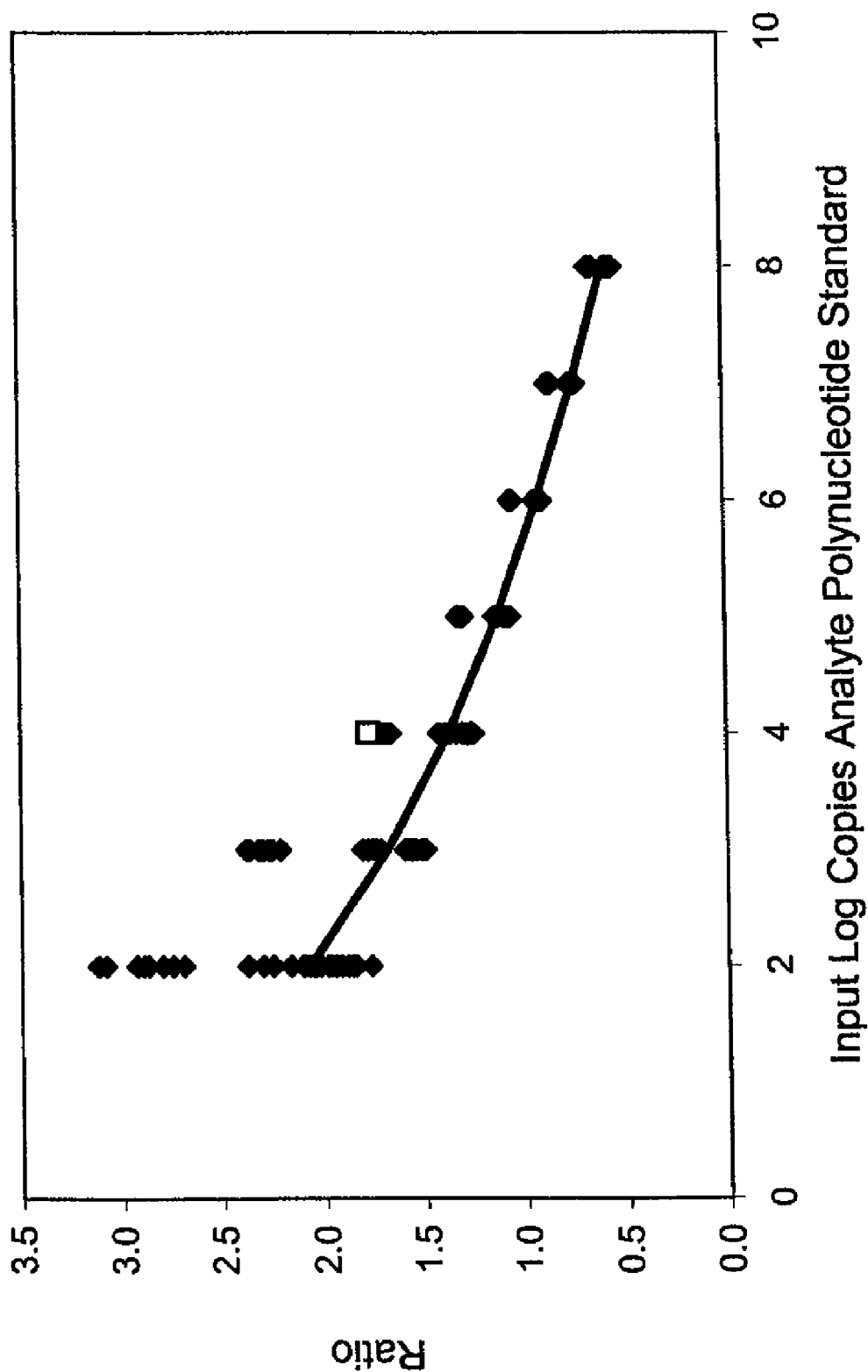
FIG. 6 is a graph illustrating a processed indicia master calibration curve. Filled diamonds ($\blacklozenge$) indicate individual data points representing ratios for IOA(analyte)/IOA(IC) calculated from raw data obtained using amplification/detection instruments 2-4. The solid heavy curve fitted to the collection of data points indicates the processed indicia master calibration curve. The open square ($\square$) indicates a result obtained using a model end-user instrument and an adjustment calibrator containing $10^4$ copies of analyte polynucleotide standard and 30,000 copies of internal calibrator.

A processed indicia master calibration curve was prepared by dividing indicia of amplification values for analyte polynucleotide standard by indicia of amplification values for internal calibrator, with each resulting ratio being associated with the input quantity of analyte polynucleotide standard used in the respective reactions. Standard curve fitting techniques familiar to those having an ordinary level of skill in the art were used to optimize the coefficients in a 4PL equation of the type presented herein. The solved equation represented the processed indicia master calibration curve that could be adjusted using results obtained on the model end-user instrument. FIG. 6 shows individual data points obtained using three amplification/detection instruments, and the fitted curve (shown as the solid heavy curve) corresponding to the master calibration curve. Of course, the equation having the fitted coefficients that specified the master calibration curve was used in the subsequent adjustment procedure. Notably, the data used for creating the processed indicia master calibration curve shown in FIG. 6 corresponds to the results in FIG. 5 that were obtained using instruments 2-4. The processed indicia master calibration curve is also presented as the solid heavy curve (i.e., labeled "Master") in FIGS. 9 and 10.

Figure 7:
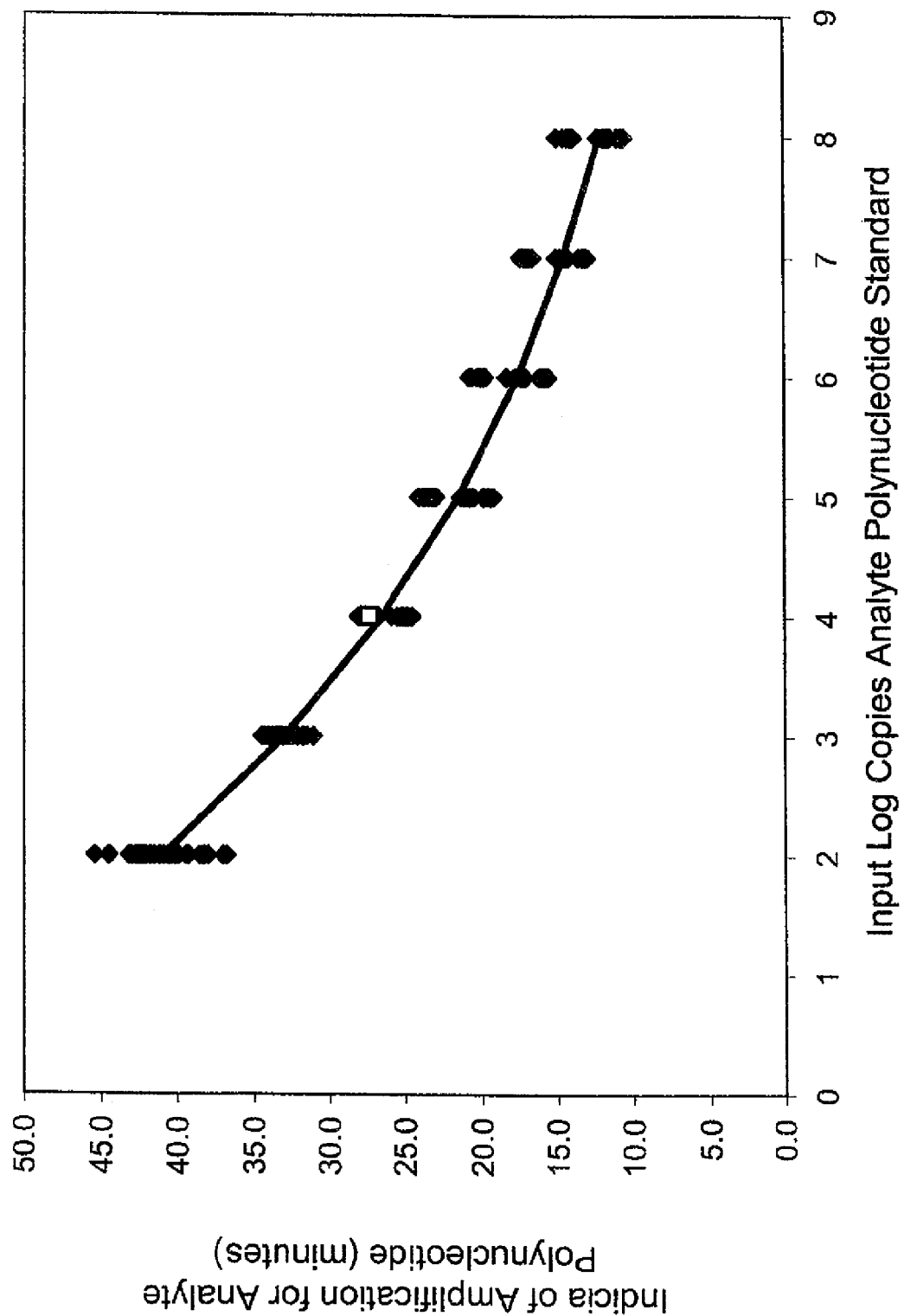
FIG. 7 is a graph illustrating a master calibration curve for analyte polynucleotide standard as a function of the starting quantity of analyte polynucleotide standard input into nucleic acid amplification reactions. Filled diamonds ($\blacklozenge$) indicate individual results obtained using amplification/detection instruments 2-4. The solid heavy curve fitted to the collection of data points indicates the master calibration curve. The open square ($\square$) indicates a result obtained using a model end-user instrument and an adjustment calibrator containing $10^4$ copies of analyte polynucleotide standard and 30,000 copies of internal calibrator. The data point indicated by the open square was not used for preparing the master curve, but was used in the subsequent adjustment procedure.
Figure 8:
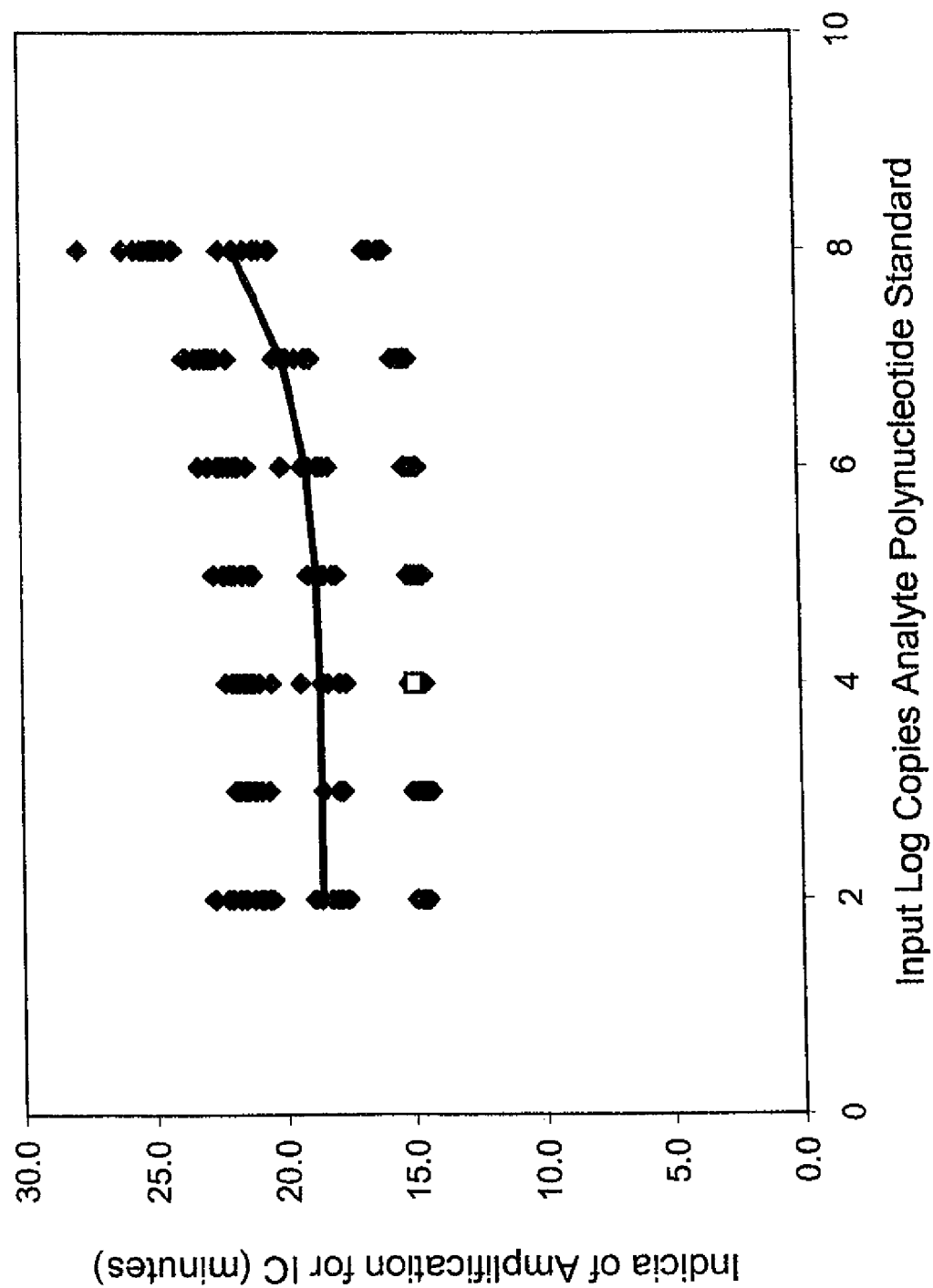
FIG. 8 is a graph illustrating a master calibration curve for internal calibrator as a function of the starting quantity of analyte polynucleotide standard input into nucleic acid amplification reactions. Filled diamonds ($\blacklozenge$) indicate individual results obtained using amplification/detection instruments 2-4. The solid heavy curve fitted to the collection of data points indicates the master calibration curve. The open square ($\square$) indicates a result obtained using a model end-user instrument and an adjustment calibrator containing $10^4$ copies of analyte polynucleotide standard and 30,000 copies of internal calibrator.

In a different procedure, separate master calibration curves for analyte polynucleotide standard and internal calibrator also were prepared. Standard curve fitting techniques familiar to those having an ordinary level of skill in the art were used separately to optimize coefficients of a 4PL equation to fit (a) the collection of indicia of amplification for the analyte polynucleotide standard as a function of the starting quantity of the analyte polynucleotide standard (i.e., Eq 1, above), and (b) the collection of indicia of amplification for the internal calibrator as a function of the starting quantity of the analyte polynucleotide standard (i.e., Eq 2, above). Data points for the indicia of amplification for internal calibrator used in the procedure correspond to the subset of data points in FIG. 2A that were obtained using instruments 2-4. Data points for the indicia of amplification for analyte polynucleotide standard used in the procedure correspond to the subset of data points in FIG. 2B that were obtained using instruments 2-4. FIG. 7 shows the data points from three instruments and the fitted curve representing the master calibration curve for indicia of amplification for analyte polynucleotide standard as a function of the starting quantity of analyte polynucleotide standard used in the amplification reactions. FIG. 8 shows the data points from three instruments and the fitted curve representing the master calibration curve for indicia of amplification for internal calibrator as a function of the starting quantity of analyte polynucleotide standard used in the amplification reactions. The fitted equations for the curves in FIGS. 7-8 specified the two master calibration curves that could be independently adjusted using results obtained on the model end-user instrument. The two adjusted calibration curves, or equations representing the adjusted curves, could then be related to each other by a mathematical operation. The solid heavy curves (i.e., labeled "Master") presented in FIGS. 11 and 12 represent the result of dividing (a) the equation for the unadjusted calibration curve for analyte polynucleotide standard by (b) the equation for the unadjusted calibration curve for internal calibrator.

The processed indicia master calibration curve shown in FIG. 6, and the independent master calibration curves shown in FIGS. 7-8 were adjusted using results from amplification of either one or two adjustment calibrators amplified on the model end-user instrument. Trials conducted using the single adjustment calibrator contained $10^4$ copies of the analyte polynucleotide standard, and 30,000 copies of internal calibrator. Trials conducted using the two-point calibration method employed adjustment calibrators containing the same constant amount of internal calibrator and either $10^3$ or $10^7$ copies of the analyte polynucleotide standard. The same nucleic acid amplification procedure used for creating the master calibration curves and the local calibration curve also was used for coamplifying the analyte polynucleotide standard and internal calibrator in the adjustment calibrators. The determined indicia of amplification for analyte polynucleotide standard and internal calibrator were used for carrying out single-point or two-point adjustments, as described herein. To simplify the graphical presentation, the open squares shown in FIGS. 6-8 indicate the results obtained using the single-point adjustment calibrator. Thus, these figures show the master calibration curves and the data points used for their determination, and additionally show results from the adjustment calibrators that were used in subsequent adjustment steps by the methods disclosed herein. The open squares in FIGS. 9 and 10 indicate the result of dividing the determined indicia of amplification for analyte polynucleotide standard by the indicia of amplification for internal calibrator. These data points were used for adjusting the processed indicia master calibration curve in the vertical dimension of the graphs to result in the dashed line labeled "Ratio Adjusted Master" in FIGS. 9 and 10. Although the separate indicia of amplification for (a) analyte polynucleotide standard and (b) internal calibrator determined from the adjustment calibrator amplification reactions on the model end-user instrument were used for independently adjusting the two master calibration curves (e.g., see FIGS. 7-8), open squares representing the calculated ratios of these values are presented on the single plots shown in FIGS. 11 and 12. This is intended to convey that a result falling on the local calibration curve was used in the independent adjustment procedure, but does not imply that the indicated data point having a ratio value was used to modify the master curve. Equations for the independently adjusted master calibration curves (e.g., FIGS. 7 and 8 representing the independent master calibration curves prior to any adjustment) were divided by each other (i.e., the equation representing the adjusted plot of analyte polynucleotide standard as a function of starting quantity of analyte polynucleotide standard was divided by the equation representing the adjusted plot of the internal calibrator as a function of starting quantity of analyte polynucleotide standard) using a commercially available electronic spreadsheet software program. The resulting fitted curve is identified as the "Independent Adjusted Master" in FIGS. 11 and 12.

Figure 9:
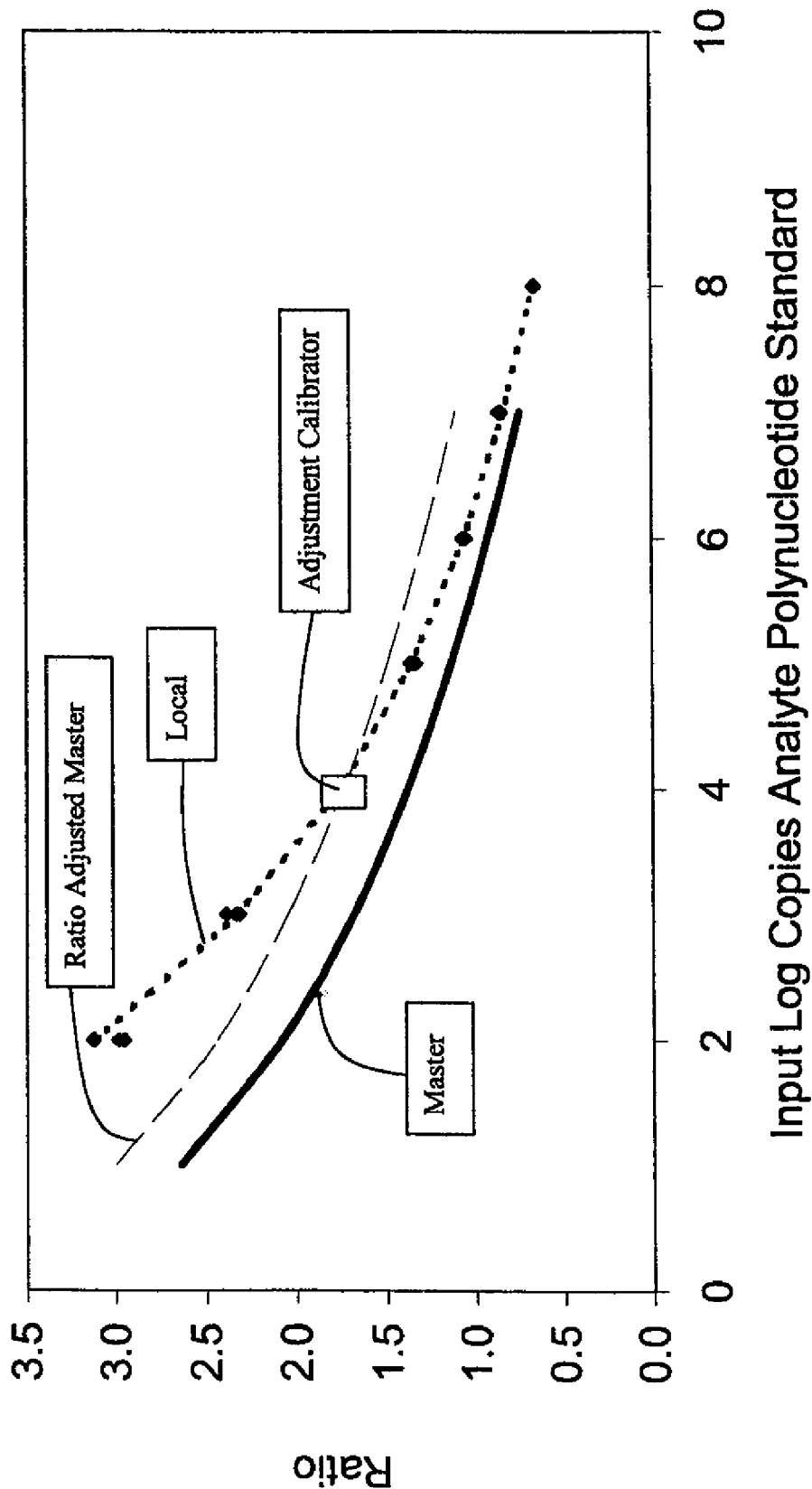
FIG. 9 is a graph showing the effect of single-point adjustment of a processed indicia master calibration curve. The heavy dotted curve (labeled "Local") indicates a local calibration curve that was established using results obtained on a model end-user instrument. Filled diamonds (♦) indicate data points used for determining the local calibration curve. The solid heavy curve (labeled "Master") indicates the processed indicia master calibration curve, also shown in FIG. 6, determined using instruments separate from the model end-user instrument. The open square (□) indicates a result, obtained using a model end-user instrument and an adjustment calibrator, used for adjusting the processed indicia master calibration curve. The dashed curve (labeled "Ratio Adjusted Master") shows the result of adjusting the processed indicia master calibration curve using a single adjustment calibrator (i.e., containing $10^4$ copies of analyte polynucleotide standard and 30,000 copies of internal calibrator) processed on the instrument used for creating the local calibration curve. The shape of the Ratio Adjusted Master curve is the same as the processed indicia master calibration curve.
Figure 10:
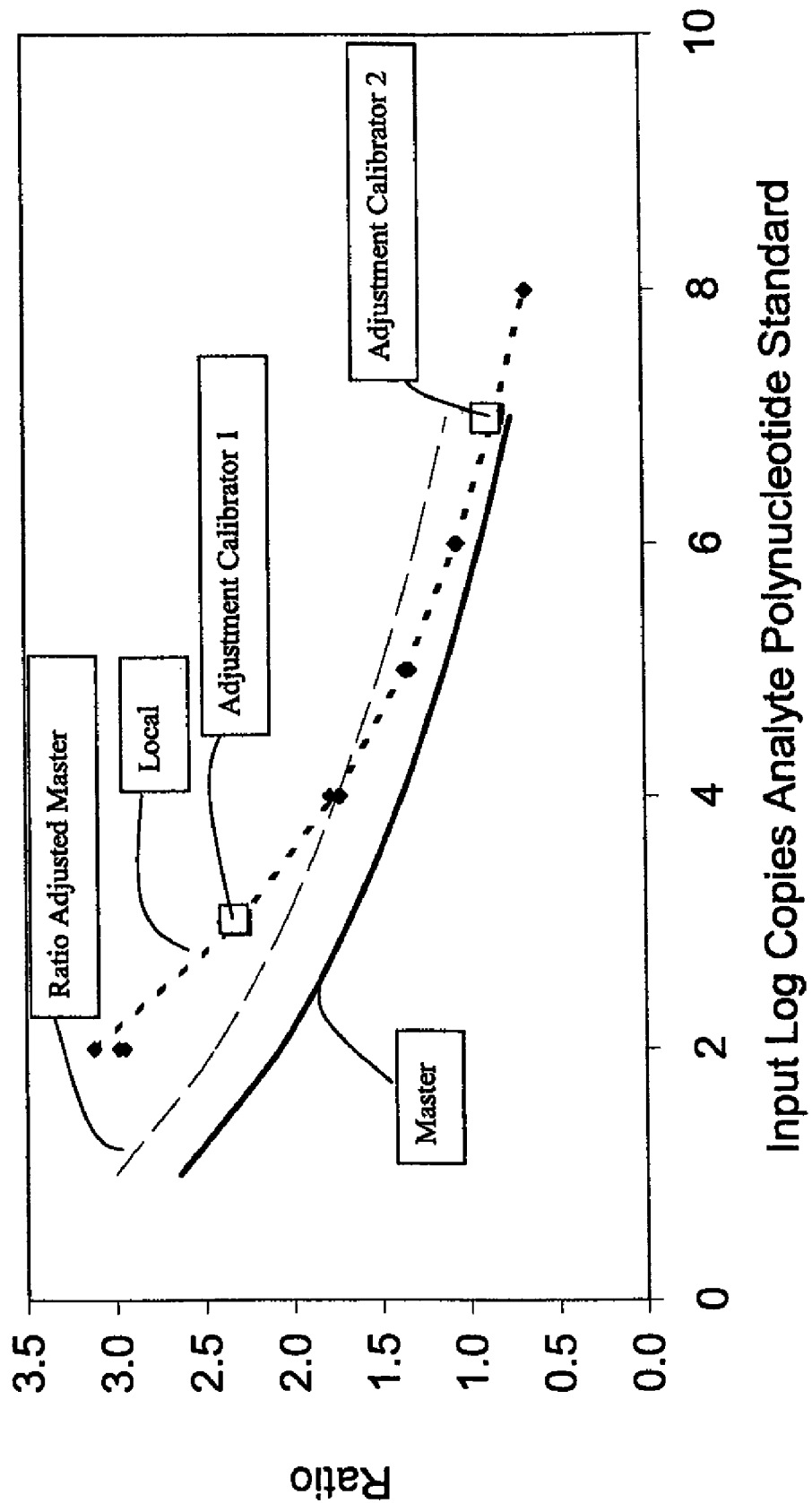
FIG. 10 is a graph showing the effect of two-point adjustment of a processed indicia master calibration curve. The heavy dotted curve (labeled "Local") indicates a local calibration curve that was established using results obtained on a model end-user instrument. Filled diamonds (♦) indicate data points used for determining the local calibration curve. The solid heavy curve (labeled "Master") indicates the processed indicia master calibration curve, also shown in FIG. 6, determined using instruments separate from the model end-user instrument. The open squares (□) indicate results, obtained using a model end-user instrument and adjustment calibrators, used for adjusting the processed indicia master calibration curve. The dashed curve (labeled "Ratio Adjusted Master") shows the result of adjusting the processed indicia master calibration curve using two adjustment calibrators (i.e., containing $10^3$ and $10^7$ copies of analyte polynucleotide standard and 30,000 copies of internal calibrator) processed on the instrument used for creating the local calibration curve. Except for a vertical shift, the shape of the Ratio Adjusted Master curve is the same as the processed indicia master calibration curve.
Figure 11:
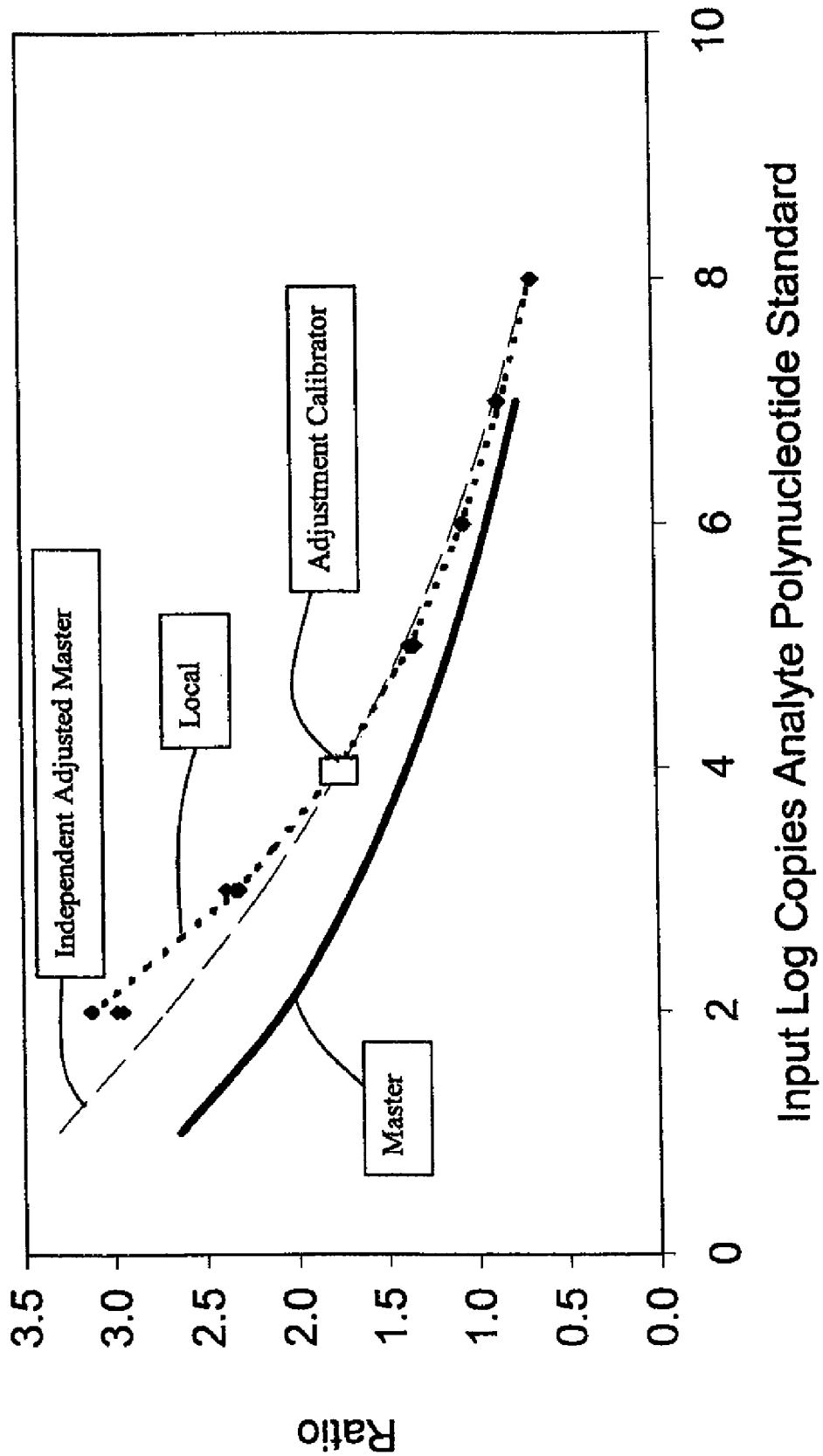
FIG. 11 is a graph showing the effect of independent adjustment of two master calibration curves, using a single-point adjustment. The heavy dotted curve (labeled "Local") indicates a local calibration curve that was established using results obtained on a model end-user instrument. Filled diamonds (♦) indicate data points used for determining the local calibration curve. The solid heavy curve (labeled "Master") indicates the result of dividing the unadjusted master calibration curve shown in FIG. 7 by the unadjusted master calibration curve shown in FIG. 8, and so represents results obtained using instruments different from the model end-user instrument. The open square (□) indicates a result obtained using a model end-user instrument and an adjustment calibrator. The dashed curve (labeled "Independent Adjusted Master") shows the result of first adjusting the individual master calibration curves determined in FIGS. 7-8 in the vertical dimension using a single adjustment calibrator (i.e., containing $10^4$ copies of analyte polynucleotide standard and 30,000 copies of internal calibrator) processed on the instrument used for creating the local calibration curve. The two adjusted curves were then related to each other by dividing the equation for the adjusted curve for analyte polynucleotide standard by the equation for the adjusted curve for internal calibrator, each as a function of the starting quantity of analyte polynucleotide standard used in the reactions. The shape of the Independent Adjusted Master curve is different from the shape of the curve resulting from the ratio of the individual unadjusted master calibration curves, and more closely approximates the local calibration curve.
Figure 12:
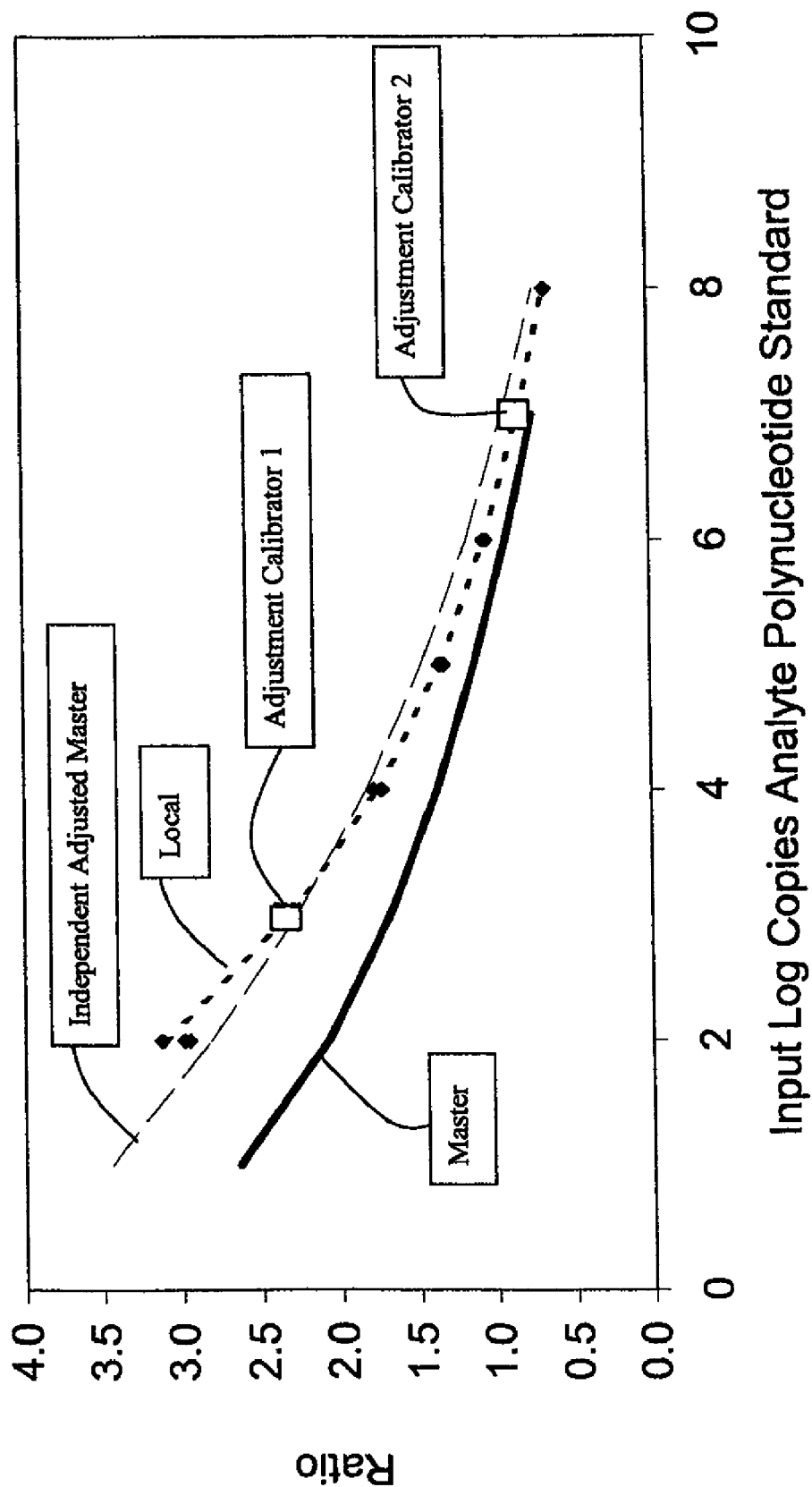
FIG. 12 is a graph showing the effect of independent adjustment of two master calibration curves, using a two-point adjustment. The heavy dotted curve (labeled "Local") indicates a local calibration curve that was established using results obtained on a model end-user instrument. Filled diamonds (♦) indicate data points used for determining the local calibration curve. The solid heavy curve (labeled "Master") indicates the result of dividing the unadjusted master calibration curve shown in FIG. 7 by the unadjusted master calibration curve shown in FIG. 8, and so represents results obtained using instruments different from the model end-user instrument. The open squares (□) indicate results obtained using a model end-user instrument and an adjustment calibrator. The dashed curve (labeled "Independent Adjusted Master") shows the result of first adjusting the individual master calibration curves determined in FIGS. 7-8 in the vertical dimension using two adjustment calibrators (i.e., containing $10^3$ and $10^7$ copies of analyte polynucleotide standard and 30,000 copies of internal calibrator) processed on the instrument used for creating the local calibration curve. The two adjusted curves were then related to each other by dividing the equation for the adjusted curve for analyte polynucleotide standard by the equation for the adjusted curve for internal calibrator, each as a function of the starting quantity of analyte polynucleotide standard used in the reactions. The shape of the Independent Adjusted Master curve is different from the shape of the curve resulting from the ratio of the individual unadjusted master calibration curves, and more closely approximates the local calibration curve.

Comparison of FIGS. 9 and 11, and comparison of FIGS. 10 and 12 revealed a fundamental distinction between the adjustment procedures based on the processed indicia master calibration curve and the independent adjustment of separate master curves (i.e., one for indicia of amplification for analyte polynucleotide standard as a function of the starting quantity of analyte polynucleotide standard, and a second for indicia of amplification for internal calibrator as a function of the starting quantity of analyte polynucleotide standard). More particularly, the method based on adjustment of the processed indica master calibration curve simply adjusted the curve in the vertical dimension without changing the shape of the processed indicia master calibration curve, as expected. In contrast, the method based on independent adjustment of two master calibration curves, followed by a step for relating the adjusted curves (e.g., the equations representing the adjusted curves), unexpectedly changed the shape of the master calibration curve such that the result more closely approximated the local calibration curve. The improvement due to this effect is evident from the results in Tables 1-2.

Table 1 presents results obtained by adjusting the master calibration curves using only a single adjustment calibrator. The first column in the table indicates the number of log copies of analyte polynucleotide standard used in each amplification reaction (n=4). Remaining columns in the table indicate the "Determined Log Copy" numbers (i.e., values calculated using the fitted equations), and % Recovery (i.e., values calculated by dividing determined values by predicted values) for quantitated values calculated using each of (a) the local calibration curve, (b) the independently adjusted master curves related to each other by the process of division to establish a ratio relationship, and (c) the adjusted processed indicia master calibration curve. As will be apparent from reviewing the tabulated data, the independent adjustment method yielded superior quantitation over the tested range of input analyte polynucleotide standard amounts. Indeed, results determined using the independent adjustment method closely approximated results calculated using the local calibration curve, with the % recovery deviating from the predicted log copy number by just over one-half log at the 100 copy level. Outstanding results were achieved at the higher levels of starting analyte polynucleotide standard. The relative improvement characteristic of the independent adjustment method is attributed to the ability of the system to change the shape of the adjusted curve when compared to the unadjusted curve.

TABLE 1

Single Point Adjusted Master Calibration Curves

| | Local Cal Curve | | Independent Adjustment | | Processed Indicia Adjustment | |
|---|---|---|---|---|---|---|
| Predicted Log Copy | Determined Log Copy | Recovery | Determined Log Copy | Recovery | Determined Log Copy | Recovery |
| 2.00 | 2.08 | 104% | 1.44 | 72% | 1.02 | 51% |
| 3.00 | 2.97 | 99% | 2.69 | 90% | 2.30 | 77% |
| 5.00 | 5.02 | 100% | 5.15 | 103% | 5.68 | 114% |
| 6.00 | 5.99 | 100% | 6.18 | 103% | 7.30 | 122% |
| 7.00 | 6.92 | 99% | 7.09 | 101% | 8.70 | 124% |
| 8.00 | 8.04 | 101% | 8.11 | 101% | 10.25 | 128% |

The results presented in Table 2 confirmed that the independent adjustment method, when compared with the method of adjusting a processed indicia calibration curve, yielded superior results more closely approximating the local calibration curve. When compared with the single point adjustment trials, the two point independent adjustment protocol showed improved recovery at the lowest level of input analyte polynucleotide standard while yielding very good results over the full tested range.

TABLE 2

Two Point Adjusted Master Calibration Curves

| | Local Cal Curve | | Independent Adjustment | | Processed Indicia Adjustment | |
|---|---|---|---|---|---|---|
| Predicted Log Copy | Determined Log Copy | Recovery | Determined Log Copy | Recovery | Determined Log Copy | Recovery |
| 2.00 | 2.08 | 104% | 1.62 | 81% | 1.02 | 51% |
| 4.00 | 4.02 | 100% | 4.22 | 105% | 4.02 | 100% |
| 5.00 | 5.02 | 100% | 5.40 | 108% | 5.70 | 114% |
| 6.00 | 5.99 | 100% | 6.46 | 108% | 7.33 | 122% |
| 8.00 | 8.04 | 101% | 8.42 | 105% | 10.30 | 129% |

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A method of establishing an equation for an adjusted calibration curve, said method comprising the steps of:
    (a) obtaining a plurality of standard samples, each containing a constant starting quantity of an internal calibrator and a known starting quantity of an analyte polynucleotide standard;
    (b) coamplifying the internal calibrator and the analyte polynucleotide standard in each of the plurality of standard samples;
    (c) determining for each of the plurality of standard samples indicia of amplification for the internal calibrator and the analyte polynucleotide standard that coamplified, whereby there is obtained
        a collection of determined indicia of amplification for the internal calibrator as a function of the known starting quantity of the analyte polynucleotide standard, and
        a collection of determined indicia of amplification for the analyte polynucleotide standard as a function of the known starting quantity of the analyte polynucleotide standard;
    (d) optimizing a first equation to fit a first curve to the collection of determined indicia of amplification for the internal calibrator as a function of the known starting quantity of the analyte polynucleotide standard, thereby resulting in a first fitted equation;

(e) optimizing a second equation to fit a second curve to the collection of determined indicia of amplification for the analyte polynucleotide standard as a function of the known starting quantity of the analyte polynucleotide standard, thereby resulting in a second fitted equation;

(f) obtaining an adjustment calibrator comprising a predetermined quantity of the analyte polynucleotide standard and said constant starting quantity of the internal calibrator;

(g) coamplifying the internal calibrator and the analyte polynucleotide standard of the adjustment calibrator;

(h) determining for the adjustment calibrator indicia of amplification for the internal calibrator and the analyte polynucleotide standard that coamplified;

(i) modifying the first fitted equation using the indicia of amplification determined for the internal calibrator of the adjustment calibrator, whereby there results an adjusted first fitted equation for fitted indicia of amplification for the internal calibrator as a function of the known starting quantity of the analyte polynucleotide standard;

(j) modifying the second fitted equation using the indicia of amplification determined for the analyte polynucleotide of the adjustment calibrator, whereby there results an adjusted second fitted equation for fitted indicia of amplification for the analyte polynucleotide standard as a function of the known starting quantity of the analyte polynucleotide standard; and (k) establishing the equation for the adjusted calibration curve by mathematically relating to each other the adjusted first fitted equation, and the adjusted second fitted equation.

2. The method of claim 1, wherein coamplifying steps (b) and (g) comprise coamplifying isothermally.

3. The method of claim 2, wherein coamplifying isothermally comprises coamplifying isothermally in a transcription-associated amplification reaction that comprises an RNA polymerase.

4. The method of claim 1, wherein coamplifying steps (b) and (g) are performed on different instruments.

5. The method of claim 1,
wherein coamplifying step (b) comprises coamplifying in a nucleic acid amplification reaction performed on a first instrument,
wherein coamplifying step (g) comprises coamplifying in a nucleic acid amplification reaction performed on a second instrument, and
wherein the first and second fitted equations of optimizing steps (d) and (e) are stored in a computer memory device linked to the second instrument.

6. The method of claim 5, wherein establishing step (k) comprises establishing the equation for the adjusted calibration curve for use on the second instrument.

7. The method of claim 1,
wherein coamplifying step (b) comprises coamplifying in an isothermal nucleic acid amplification reaction performed on a first instrument,
wherein coamplifying step (g) comprises coamplifying in an isothermal nucleic acid amplification reaction performed on a second instrument; and
wherein the first and second fitted equations of optimizing steps (d) and (e) are stored in a computer memory device linked to the second instrument.

8. The method of claim 7, wherein the first and second fitted equations of steps (d) and (e) each comprise a plurality of coefficients, and wherein obtaining step (f) further comprises obtaining the plurality of coefficients for the respective first and second fitted equations.

9. The method of claim 7, wherein the first and second equations of optimizing steps (d) and (e) are non-linear equations, each comprising a plurality of coefficients.

10. The method of claim 9, wherein the process of mathematically relating to each other in establishing step (k) comprises mathematically relating numerical results calculated using the adjusted second fitted equation and numerical results calculated using the adjusted first fitted equation as a ratio.

11. The method of claim 9, wherein the isothermal nucleic acid amplification reactions of coamplifying steps (b) and (g) each comprise a primer that amplifies both the analyte polynucleotide standard and the internal calibrator.

12. The method of claim 9, wherein the isothermal nucleic acid amplification reactions of coamplifying steps (b) and (g) comprise primers that amplify both the analyte polynucleotide standard and the internal calibrator, and do not comprise primers that amplify only the analyte polynucleotide standard or the internal calibrator.

13. The method of claim 9, wherein the isothermal nucleic acid amplification reactions of coamplifying steps (b) and (g) do not comprise any primer that amplifies both the analyte polynucleotide standard and the internal calibrator.

14. The method of claim 9, wherein coamplifying steps (b) and (g) result in the synthesis of analyte polynucleotide standard amplicons and internal calibrator amplicons, and wherein the analyte polynucleotide standard amplicons and the internal calibrator amplicons are different lengths.

15. The method of claim 9, wherein coamplifying steps (b) and (g) result in the synthesis of analyte polynucleotide standard amplicons and internal calibrator amplicons, and wherein the analyte polynucleotide standard amplicons and the internal calibrator amplicons comprise different percentages of G+C bases.

16. The method of claim 1, wherein the first fitted equation of optimizing step (d) comprises a plurality of first fitted equation coefficients, and wherein the second fitted equation of optimizing step (e) comprises a plurality of second fitted equation coefficients.

17. The method of claim 1, wherein the process of mathematically relating to each other in establishing step (k) comprises mathematically relating numerical results calculated using the adjusted second fitted equation and numerical results calculated using the adjusted first fitted equation as a ratio.

18. The method of claim 1, wherein the process of mathematically relating to each other in establishing step (k) comprises mathematically relating numerical results calculated using the adjusted second fitted equation and numerical results calculated using the adjusted first fitted equation as a difference.

19. The method of claim 1, wherein modifying step (i) comprises
determining an adjustment factor for internal calibrator using
the indicia of amplification determined for the internal calibrator of the adjustment calibrator, and
a value calculated by solving the first fitted equation at the starting quantity of analyte polynucleotide equal to the predetermined quantity of the analyte polynucleotide standard of the adjustment calibrator; and adding the adjustment factor for internal calibrator to one coefficient of the first fitted equation;
and wherein modifying step (j) comprises
determining an adjustment factor for analyte polynucleotide using
the indicia of amplification determined for the analyte polynucleotide standard of the adjustment calibrator, and
a value calculated by solving the second fitted equation at the starting quantity of analyte polynucleotide equal to the predetermined quantity of the analyte polynucleotide standard of the adjustment calibrator; and
adding the adjustment factor for analyte polynucleotide to one coefficient of the second fitted equation.

20. The method of claim 1, wherein coamplifying steps (b) and (g) each comprise coamplifying in a nucleic acid amplification reaction that comprises a primer that amplifies both the analyte polynucleotide standard and the internal calibrator.

21. The method of claim 1, wherein coamplifying steps (b) and (g) each comprise coamplifying in a nucleic acid amplification reaction that comprises primers that amplify both the analyte polynucleotide standard and the internal calibrator, and does not comprise primers that amplify only the analyte polynucleotide standard or the internal calibrator.

22. The method of claim 1, wherein coamplifying steps (b) and (g) each comprise coamplifying in a nucleic acid amplification reaction that does not comprise any primer that amplifies both the analyte polynucleotide standard and the internal calibrator.

23. The method of claim 1, further comprising steps for
obtaining a second adjustment calibrator comprising a second predetermined quantity of the analyte polynucleotide standard and said constant quantity of the internal calibrator;
coamplifying the internal calibrator and the analyte polynucleotide standard of the second adjustment calibrator;
determining for the second adjustment calibrator indicia of amplification for the internal calibrator and the analyte polynucleotide standard that coamplified; and
modifying the first and second fitted equations using respectively the indicia of amplification for the internal calibrator of the second adjustment calibrator and the analyte polynucleotide standard of the second adjustment calibrator.

24. The method of claim 1, wherein coamplifying steps (b) and (g) result in the synthesis of an analyte polynucleotide standard amplicon and an internal calibrator amplicon, and wherein the analyte polynucleotide standard amplicon and the internal calibrator amplicon are different lengths.

25. The method of claim 1, wherein coamplifying steps (b) and (g) result in the synthesis of an analyte polynucleotide standard amplicon and an internal calibrator amplicon, and wherein the analyte polynucleotide standard amplicon and the internal calibrator amplicon comprise different percentages of G+C bases.

26. The method of claim 1, wherein the first and second equations of optimizing steps (d) and (e) are non-linear equations, each comprising a plurality of coefficients.

27. The method of claim 1, wherein the first and second fitted equations of steps (d) and (e) each comprise a plurality of coefficients, and wherein obtaining step (f) further comprises obtaining the respective plurality of coefficients for the first and second fitted equations.

28. A method of preparing a kit comprising a calibrator for adjusting a stored master calibration curve, said method comprising the steps of:
forming a plurality of standard samples, each containing a constant starting quantity of an internal calibrator and a known starting quantity of an analyte polynucleotide standard;
coamplifying the internal calibrator and the analyte polynucleotide standard in a nucleic acid amplification reaction for each of the plurality of standard samples;
determining indicia of amplification for the internal calibrator and the analyte polynucleotide standard that coamplified in each nucleic acid amplification reaction, whereby there is obtained
a collection of determined indicia of amplification for the internal calibrator as a function of the known starting quantity of the analyte polynucleotide standard, and
a collection of determined indicia of amplification for the analyte polynucleotide standard as a function of the known starting quantity of the analyte polynucleotide standard;
optimizing a first equation to fit a first curve to the collection of determined indicia of amplification for the internal calibrator as a function of the known starting quantity of the analyte polynucleotide standard, thereby resulting in a first fitted equation comprising a set of first fitted equation coefficients;
optimizing a second equation to fit a second curve to the collection of determined indicia of amplification for the analyte polynucleotide standard as a function of the known starting quantity of the analyte polynucleotide standard, thereby resulting in a second fitted equation comprising a set of second fitted equation coefficients; and
preparing a packaged combination comprising
(a) a tangible form of the set of first fitted equation coefficients,
(b) a tangible form of the set of second fitted equation coefficients, and
(c) an adjustment calibrator that comprises
a predetermined amount of the analyte polynucleotide standard, and
said constant starting quantity of the internal calibrator.

29. The method of claim 28, wherein the nucleic acid amplification reaction of the step for coamplifying is an isothermal nucleic acid amplification reaction.

30. The method of claim 29, wherein the isothermal nucleic acid amplification reaction is a transcription-associated amplification reaction comprising an RNA polymerase.

31. The method of claim 28, wherein the nucleic acid amplification reaction of the step for coamplifying comprises a primer that amplifies both the analyte polynucleotide standard and the internal calibrator.

32. The method of claim 28, wherein the nucleic acid amplification reaction of the step for coamplifying comprises primers that amplify both the analyte polynucleotide standard and the internal calibrator, and do not comprise primers that amplify only the analyte polynucleotide standard or the internal calibrator.

33. The method of claim 28, wherein the nucleic acid amplification reaction of the step for coamplifying does not comprise any primer that amplifies both the analyte polynucleotide standard and the internal calibrator.

34. The method of claim 28, wherein the step for determining indicia of amplification comprises determining time-dependent indicia of amplification.

35. The method of claim 28, wherein the first and second equations of the steps for optimizing are first and second non-linear equations.

36. The method of claim 28, wherein the tangible forms of the sets of first and second fitted equation coefficients comprise machine-readable forms of the sets of first and second fitted equation coefficients.

37. The method of claim 36, wherein the machine-readable forms of the sets of first and second fitted equation coefficients comprise a barcode.

38. The method of claim 28, wherein the coamplifying step produces an internal calibrator amplicon and an analyte polynucleotide standard amplicon, and wherein the internal calibrator amplicon and the analyte polynucleotide standard amplicon are different lengths.

39. The method of claim 28, wherein the coamplifying step produces an internal calibrator amplicon and an analyte polynucleotide standard amplicon, and wherein the internal calibrator amplicon and the analyte polynucleotide standard amplicon comprise different percentages of G+C bases.

40. The method of claim 28, wherein the packaged combination of the step for preparing further comprises a second adjustment calibrator that comprises a second predetermined starting quantity of the analyte polynucleotide standard and said constant starting quantity of the internal calibrator.

41. The method of claim 28, wherein the nucleic acid amplification reaction of the step for coamplifying is an isothermal nucleic acid amplification reaction, and wherein the first and second equations of the steps for optimizing are first and second non-linear equations.

42. The method of claim 41, wherein the nucleic acid amplification reaction of the step for coamplifying comprises a primer that amplifies both the analyte polynucleotide standard and the internal calibrator.

43. The method of claim 41, wherein the nucleic acid amplification reaction of the step for coamplifying comprises primers that amplify both the analyte polynucleotide standard and the internal calibrator, and does not comprise primers that amplify only the analyte polynucleotide standard or the internal calibrator.

44. The method of claim 41, wherein the nucleic acid amplification reaction of the step for coamplifying does not comprise any primer that amplifies both the analyte polynucleotide standard and the internal calibrator.

45. The method of claim 41, wherein the coamplifying step produces an internal calibrator amplicon and an analyte polynucleotide standard amplicon, and wherein the internal calibrator amplicon and the analyte polynucleotide standard amplicon comprise different percentages of G+C bases.

46. The method of claim 41, wherein the coamplifying step produces an internal calibrator amplicon and an analyte polynucleotide standard amplicon, and wherein the internal calibrator amplicon and the analyte polynucleotide standard amplicon are different lengths.

47. The method of claim 46, wherein the nucleic acid amplification reaction of the step for coamplifying comprises a primer that amplifies both the analyte polynucleotide standard and the internal calibrator.

48. The method of claim 46, wherein the nucleic acid amplification reaction of the step for coamplifying comprises primers that amplify both the analyte polynucleotide standard and the internal calibrator, and does not comprise primers that amplify only the analyte polynucleotide standard or the internal calibrator.

49. The method of claim 46, wherein the nucleic acid amplification reaction of the step for coamplifying does not comprise any primer that amplifies both the analyte polynucleotide standard and the internal calibrator.

50. A method of preparing an equation for quantifying analyte polynucleotide in multiplex nucleic acid amplification reactions that comprise a constant amount of internal calibrator, said method comprising the steps of:
  obtaining a plurality of coefficients of a first stored master curve equation that specifies indicia of amplification for analyte polynucleotide standard as a function of the starting quantity of analyte polynucleotide standard input into nucleic acid amplification reactions;
  obtaining a plurality of coefficients of a second stored master curve equation that specifies indicia of amplification for internal calibrator as a function of the starting quantity of analyte polynucleotide standard input into nucleic acid amplification reactions;
  performing a nucleic acid amplification reaction using an adjustment calibrator that comprises a known amount of analyte polynucleotide standard and said constant starting amount of internal calibrator, wherein said nucleic acid amplification reaction coamplifies analyte polynucleotide standard and internal calibrator of the adjustment calibrator, and wherein said nucleic acid amplification reaction produces an analyte polynucleotide standard amplicon and an internal calibrator amplicon;
  determining indicia of amplification for analyte polynucleotide standard and internal calibrator that coamplified in the nucleic acid amplification reaction;
  establishing an adjustment factor for analyte polynucleotide standard using
    indicia of amplification for analyte polynucleotide standard determined from the nucleic acid amplification reaction, and
    a value calculated by solving the first stored master curve equation at the starting quantity of analyte polynucleotide standard equal to the known amount of analyte polynucleotide standard of the adjustment calibrator;
  establishing an adjustment factor for internal calibrator using
    indicia of amplification for internal calibrator determined from the nucleic acid amplification reaction, and
    a value calculated by solving the second stored master curve equation at the starting quantity of analyte polynucleotide standard equal to the known amount of analyte polynucleotide standard of the adjustment calibrator;
  modifying one coefficient of the first stored master curve equation using the adjustment factor for analyte polynucleotide standard, whereby there results an equation specifying an adjusted calibration curve for analyte polynucleotide standard;
  modifying one coefficient of the second stored master curve equation using the adjustment factor for internal calibrator, whereby there results an equation specifying an adjusted calibration curve for internal calibrator; and
  preparing the equation for quantifying analyte polynucleotide by mathematically relating to each other
    (a) the equation specifying the adjusted calibration curve for analyte polynucleotide standard, and
    (b) the equation specifying the adjusted calibration curve for internal calibrator.

51. The method of claim 50, wherein the step for performing the nucleic acid amplification reaction comprises performing an isothermal nucleic acid amplification reaction.

52. The method of claim 51, wherein the isothermal nucleic acid amplification reaction is a transcription-associated amplification reaction comprising an RNA polymerase.

53. The method of claim 50, wherein the analyte polynucleotide standard amplicon and the internal calibrator amplicon of the step for performing the nucleic acid amplification reaction are different lengths.

54. The method of claim 50, wherein the analyte polynucleotide standard amplicon and the internal calibrator amplicon of the step for performing the nucleic acid amplification reaction comprise different percentages of G+C bases.

55. The method of claim 50,
wherein the step for performing comprises performing on a first nucleic acid amplification instrument said nucleic acid amplification reaction, and
wherein the plurality of coefficients of the first stored master curve equation and the plurality of coefficients of the second stored master curve equation of the steps for obtaining are not determined using the first nucleic acid amplification instrument.

56. The method of claim 50, wherein the step for determining indicia of amplification comprises determining time-dependent indicia of amplification.

57. The method of claim 50, wherein the first and second stored master curve equations are non-linear equations.

58. The method of claim 50, wherein the nucleic acid amplification reaction of the step for performing comprises at least one primer that amplifies both internal calibrator and analyte polynucleotide standard.

59. The method of claim 50, wherein the nucleic acid amplification reaction of the step for performing comprises shared primers, and does not comprise any primer that amplifies internal calibrator without also amplifying analyte polynucleotide standard.

60. The method of claim 50, wherein the nucleic acid amplification reaction of the step for performing does not comprise any shared primer that amplifies both internal calibrator and analyte polynucleotide standard.

61. The method of claim 50, wherein the step for preparing the equation for quantifying analyte polynucleotide comprises mathematically relating by division to determine a ratio.

62. The method of claim 50, wherein the step for preparing the equation for quantifying analyte polynucleotide comprises mathematically relating by subtraction to determine a difference.

63. The method of claim 61, wherein the step for performing the nucleic acid amplification reaction comprises performing an isothermal nucleic acid amplification reaction, and wherein the first and second stored master curve equations are non-linear equations.

64. The method of claim 63, wherein the nucleic acid amplification reaction of the step for performing comprises at least one primer that amplifies both internal calibrator and analyte polynucleotide standard.

65. The method of claim 63, wherein the nucleic acid amplification reaction of the step for performing comprises shared primers, and does not comprise any primer that amplifies internal calibrator without also amplifying analyte polynucleotide standard.

66. The method of claim 63, wherein the nucleic acid amplification reaction of the step for performing does not comprise any shared primer that amplifies both internal calibrator and analyte polynucleotide standard.

67. The method of claim 63, wherein the analyte polynucleotide standard amplicon and the internal calibrator amplicon of the step for performing the nucleic acid amplification reaction comprise different percentages of G+C bases.

68. The method of claim 63, wherein the analyte polynucleotide standard amplicon and the internal calibrator amplicon of the step for performing the nucleic acid amplification reaction are different lengths.

69. The method of claim 68, wherein the nucleic acid amplification reaction of the step for performing comprises at least one primer that amplifies both internal calibrator and analyte polynucleotide standard.

70. The method of claim 68, wherein the nucleic acid amplification reaction of the step for performing comprises shared primers, and does not comprise any primer that amplifies internal calibrator without also amplifying analyte polynucleotide standard.

71. The method of claim 68, wherein the nucleic acid amplification reaction of the step for performing does not comprise any shared primer that amplifies both internal calibrator and analyte polynucleotide standard.

72. The method of claim 50, wherein the step for preparing the equation for quantifying analyte polynucleotide comprises mathematically relating
numerical values calculated using the equation specifying the adjusted calibration curve for analyte polynucleotide standard, and
numerical values calculated using the equation specifying the adjusted calibration curve for internal calibrator.

73. The method of claim 72, wherein the step for preparing the equation for quantifying analyte polynucleotide comprises mathematically relating by division to calculate a ratio.

74. The method of claim 72, wherein the step for preparing the equation for quantifying analyte polynucleotide comprises mathematically relating by subtraction to calculate a difference.

75. The method of claim 50, wherein the step for performing the nucleic acid amplification reaction comprises performing an isothermal nucleic acid amplification reaction, and wherein the first and second stored master curve equations are non-linear equations.

76. The method of claim 75, wherein the nucleic acid amplification reaction of the step for performing comprises at least one primer that amplifies both internal calibrator and analyte polynucleotide standard.

77. The method of claim 75, wherein the nucleic acid amplification reaction of the step for performing comprises shared primers, and does not comprise any primer that amplifies internal calibrator without also amplifying analyte polynucleotide standard.

78. The method of claim 75, wherein the nucleic acid amplification reaction of the step for performing does not comprise any shared primer that amplifies both internal calibrator and analyte polynucleotide standard.

79. The method of claim 75, wherein the analyte polynucleotide standard amplicon and the internal calibrator amplicon of the step for performing the nucleic acid amplification reaction comprise different percentages of G+C bases.

80. The method of claim 75, wherein the analyte polynucleotide standard amplicon and the internal calibrator amplicon of the step for performing the nucleic acid amplification reaction are different lengths.

81. The method of claim 80, wherein the nucleic acid amplification reaction of the step for performing comprises at least one primer that amplifies both internal calibrator and analyte polynucleotide standard.

82. The method of claim 80, wherein the nucleic acid amplification reaction of the step for performing comprises shared primers, and does not comprise any primer that amplifies internal calibrator without also amplifying analyte polynucleotide standard.

83. The method of claim 80, wherein the nucleic acid amplification reaction of the step for performing does not comprise any shared primer that amplifies both internal calibrator and analyte polynucleotide standard.

* * * * *